(12) United States Patent
Melvin et al.

(10) Patent No.: US 7,658,705 B2
(45) Date of Patent: Feb. 9, 2010

(54) ACTUATION MECHANISMS FOR A HEART ACTUATION DEVICE

(75) Inventors: David Boyd Melvin, Loveland, OH (US); Geoffrey Nay, Cincinnati, OH (US)

(73) Assignee: Cardioenergetics, Inc., Cincinnati, OH (US)

( * ) Notice: Subject to any disclaimer, the term of this patent is extended or adjusted under 35 U.S.C. 154(b) by 306 days.

(21) Appl. No.: 11/298,430

(22) Filed: Dec. 8, 2005

(65) Prior Publication Data

US 2006/0155160 A1    Jul. 13, 2006

Related U.S. Application Data

(63) Continuation of application No. PCT/US2004/018277, filed on Jun. 9, 2004.

(60) Provisional application No. 60/477,077, filed on Jun. 9, 2003.

(51) Int. Cl.
*A61M 1/12* (2006.01)
(52) U.S. Cl. .......................... 600/16; 600/37
(58) Field of Classification Search ............. 600/16–18, 600/37
See application file for complete search history.

(56) References Cited

U.S. PATENT DOCUMENTS

| 2,826,193 A | 3/1958 | Arthur |
| 3,053,249 A | 9/1962 | Smith |
| 3,176,316 A | 4/1965 | Bodell |
| 3,455,298 A | 7/1969 | Anstadt |
| 3,513,836 A | 5/1970 | Sausse |

(Continued)

FOREIGN PATENT DOCUMENTS

EP    0119357    3/1987

(Continued)

OTHER PUBLICATIONS

Farrar, et al. (1992), "A New Skeletal Linear-pull Energy Convertor as a Power Source for Prosthetic Circulatory Support Devices", Journal of Heart and Lung Transplantation, pp. S341-S349.

(Continued)

*Primary Examiner*—Carl H Layno
*Assistant Examiner*—Brian T Gedeon
(74) *Attorney, Agent, or Firm*—Wood, Herron & Evans, LLP

(57) ABSTRACT

An actuation mechanism for assisting the operation of the natural heart has a varying shape for deforming the heart. In one embodiment, a plurality of links articulates with respect to each other for varying the shape of the actuation mechanism. The plurality of links is configured for being positioned proximate to an outer surface of the heart for deforming the heart by varying the shape of the actuation mechanism. In another embodiment, a jacket for coupling with an outer surface of the heart has a tether coupled to successive sections of the jacket. The tether is operable to be translated with respect to the jacket sections to vary the shape of the jacket for deforming the heart. In another embodiment, a plurality of concentric ring structures are coupled together to move with respect to each other in a concentric fashion. A movement mechanism coupled to the rings is operable to vary their positions with respect to each other to vary the overall shape for deforming the heart.

14 Claims, 16 Drawing Sheets

U.S. PATENT DOCUMENTS

| | | | |
|---|---|---|---|
| 3,590,815 A | 7/1971 | Shiff | |
| 3,613,672 A | 10/1971 | Schiff | |
| 3,668,708 A | 6/1972 | Tindal | |
| 3,713,439 A | 1/1973 | Cabezudo | |
| 3,791,388 A | 2/1974 | Rosen et al. | |
| 3,827,426 A | 8/1974 | Page et al. | |
| 3,835,864 A | 9/1974 | Rasor et al. | |
| 3,983,863 A | 10/1976 | Janke et al. | |
| 4,149,277 A | 4/1979 | Bokros | |
| 4,187,558 A | 2/1980 | Dahlen et al. | |
| 4,192,293 A | 3/1980 | Asrican | |
| 4,255,820 A | 3/1981 | Rothermel et al. | |
| 4,453,537 A | 6/1984 | Spitzer | |
| 4,519,392 A | 5/1985 | Lingua | |
| 4,536,893 A | 8/1985 | Parravicini | |
| 4,585,458 A | 4/1986 | Kurland | |
| 4,597,766 A | 7/1986 | Hilal et al. | |
| 4,621,617 A | 11/1986 | Sharma | |
| 4,690,134 A | 9/1987 | Snyders | |
| 4,713,075 A | 12/1987 | Kurland | |
| 4,773,910 A | 9/1988 | Chen et al. | |
| 4,809,676 A | 3/1989 | Freeman | |
| 4,846,831 A | 7/1989 | Skillin | |
| 4,904,255 A | 2/1990 | Chareire et al. | |
| 4,917,700 A | 4/1990 | Aikins | |
| 4,936,857 A | 6/1990 | Kulik | |
| 4,946,377 A | 8/1990 | Kovach | |
| 4,957,477 A | 9/1990 | Lundback | |
| 4,964,414 A | 10/1990 | Handa et al. | |
| 5,049,155 A | 9/1991 | Bruchman et al. | |
| 5,061,283 A | 10/1991 | Silvestrini | |
| 5,109,843 A | 5/1992 | Melvin et al. | |
| 5,116,372 A | 5/1992 | Laboureau | |
| 5,119,804 A | 6/1992 | Anstadt | |
| 5,131,905 A | 7/1992 | Grooters | |
| 5,139,517 A | 8/1992 | Corral | |
| 5,169,381 A | 12/1992 | Snyders | |
| 5,192,314 A | 3/1993 | Daskalakis | |
| 5,197,983 A | 3/1993 | Berman et al. | |
| 5,201,880 A | 4/1993 | Wright et al. | |
| 5,217,495 A | 6/1993 | Kaplan et al. | |
| 5,256,132 A | 10/1993 | Snyders | |
| 5,258,021 A | 11/1993 | Duran | |
| 5,334,217 A | 8/1994 | Das | |
| 5,345,949 A | 9/1994 | Shlain | |
| 5,358,519 A | 10/1994 | Grandjean | |
| 5,370,685 A | 12/1994 | Stevens | |
| 5,383,840 A | 1/1995 | Heilman et al. | |
| 5,385,528 A | 1/1995 | Wilk | |
| 5,443,504 A | 8/1995 | Hill | |
| 5,456,715 A | 10/1995 | Liotta | |
| 5,484,391 A | 1/1996 | Buckman et al. | |
| 5,487,760 A | 1/1996 | Villafana | |
| 5,533,958 A | 7/1996 | Wilk | |
| 5,558,617 A * | 9/1996 | Heilman et al. | 600/16 |
| 5,571,176 A | 11/1996 | Taheri | |
| 5,581,176 A | 12/1996 | Lee | |
| 5,593,424 A | 1/1997 | Northrup, III | |
| 5,643,308 A | 7/1997 | Markman | |
| 5,655,548 A | 8/1997 | Nelson et al. | |
| 5,667,526 A | 9/1997 | Levin | |
| 5,697,978 A | 12/1997 | Sgro | |
| 5,702,343 A | 12/1997 | Alferness | |
| 5,709,695 A | 1/1998 | Northrup | |
| 5,713,954 A | 2/1998 | Rosenberg et al. | |
| 5,727,569 A | 3/1998 | Benetti et al. | |
| 5,738,626 A | 4/1998 | Jarvik | |
| 5,738,627 A | 4/1998 | Kovacs et al. | |
| 5,749,883 A | 5/1998 | Halpern | |
| 5,800,528 A | 9/1998 | Lederman et al. | |
| 5,824,071 A | 10/1998 | Nelson et al. | |
| 5,910,124 A | 6/1999 | Rubin | |
| 5,957,977 A | 9/1999 | Melvin | |
| 5,961,440 A | 10/1999 | Schweich et al. | |
| 5,981,827 A | 11/1999 | Devlin et al. | |
| 6,019,722 A | 2/2000 | Spence et al. | |
| 6,045,497 A | 4/2000 | Schweich et al. | |
| 6,050,936 A | 4/2000 | Schweich et al. | |
| 6,059,715 A | 5/2000 | Schweich et al. | |
| 6,077,214 A | 6/2000 | Mortier et al. | |
| 6,085,754 A | 7/2000 | Alferness et al. | |
| 6,110,100 A | 8/2000 | Talpade | |
| 6,123,662 A | 9/2000 | Alferness et al. | |
| 6,125,852 A | 10/2000 | Stevens et al. | |
| 6,162,168 A | 12/2000 | Schweich et al. | |
| 6,165,119 A | 12/2000 | Schweich et al. | |
| 6,165,120 A | 12/2000 | Schweich et al. | |
| 6,179,791 B1 | 1/2001 | Krueger | |
| 6,183,411 B1 | 2/2001 | Mortier et al. | |
| 6,214,047 B1 | 4/2001 | Melvin | |
| 6,221,103 B1 | 4/2001 | Melvin | |
| 6,260,552 B1 | 7/2001 | Mortier et al. | |
| 6,261,222 B1 | 7/2001 | Schweich, Jr. et al. | |
| 6,264,602 B1 | 7/2001 | Mortier et al. | |
| 6,293,906 B1 | 9/2001 | Vanden Hoek et al. | |
| 6,319,231 B1 | 11/2001 | Andrulitis | |
| 6,324,430 B1 | 11/2001 | Zarinetchi et al. | |
| 6,324,431 B1 | 11/2001 | Zarinetchi et al. | |
| 6,332,863 B1 | 12/2001 | Schweich, Jr. et al. | |
| 6,332,864 B1 | 12/2001 | Schweich, Jr. et al. | |
| 6,332,893 B1 | 12/2001 | Mortier et al. | |
| 6,375,611 B1 | 4/2002 | Voss et al. | |
| 6,402,680 B2 * | 6/2002 | Mortier et al. | 600/16 |
| 6,409,760 B1 | 6/2002 | Melvin | |
| 6,425,856 B1 * | 7/2002 | Shapland et al. | 600/37 |
| 6,579,226 B2 | 6/2003 | Vanden Hoek et al. | |
| 6,582,375 B2 | 6/2003 | Melvin et al. | |
| 6,592,619 B2 | 7/2003 | Melvin | |
| 6,620,095 B2 | 9/2003 | Taheri | |
| 6,733,510 B1 | 5/2004 | Melvin | |
| 6,764,510 B2 | 7/2004 | Vidlund et al. | |
| 6,988,982 B2 * | 1/2006 | Melvin et al. | 600/16 |
| 7,118,525 B2 | 10/2006 | Coleman et al. | |
| 7,361,191 B2 | 4/2008 | Melvin | |
| 2003/0023132 A1 | 1/2003 | Melvin et al. | |
| 2004/0059180 A1 | 3/2004 | Melvin | |
| 2004/0225177 A1 * | 11/2004 | Coleman et al. | 600/17 |
| 2005/0197527 A1 * | 9/2005 | Bolling | 600/37 |
| 2005/0250976 A1 | 11/2005 | Melvin | |
| 2006/0155159 A1 | 7/2006 | Melvin | |
| 2006/0178551 A1 | 8/2006 | Melvin | |
| 2006/0187550 A1 | 8/2006 | Melvin | |
| 2006/0189840 A1 * | 8/2006 | Walsh et al. | 600/16 |
| 2008/0081942 A1 * | 4/2008 | Pai et al. | 600/16 |

FOREIGN PATENT DOCUMENTS

| | | |
|---|---|---|
| EP | 0583012 | 7/1996 |
| SU | 1191076 A | 11/1985 |
| WO | WO9829041 | 7/1998 |
| WO | WO9930647 | 6/1999 |
| WO | WO9953977 | 10/1999 |
| WO | WO0002500 | 1/2000 |
| WO | WO0006026 | 2/2000 |
| WO | WO0006027 | 2/2000 |
| WO | WO0006028 | 2/2000 |
| WO | WO0016700 | 3/2000 |
| WO | WO0018320 | 4/2000 |
| WO | WO0047270 | 8/2000 |
| WO | WO0167985 | 2/2001 |
| WO | WO0128455 | 4/2001 |
| WO | WO0185061 | 11/2001 |
| WO | WO0191667 | 12/2001 |
| WO | WO0195830 | 12/2001 |

| | | |
|---|---|---|
| WO | WO0195831 | 12/2001 |
| WO | WO0195832 | 12/2001 |

OTHER PUBLICATIONS

Farrar, et al. (1995), "Mechanical Advantage of Skeletal Muscle as a Cardiac Assist Power Sources", ASAIO Journal, pp. M481-M484.

Sasaki, et al. (1992), "A Skeletal Muscle Actuator for an Artificial Heart", ASAIO Journal, pp. M507-M511.

Acker, et al. (1987), "Skeletal Muscle as the Potential Power Source for a Cardiovascular Pump; Assessment in Vivo Science", Science, vol. 236, pp. 324-327.

Salmons, et al. (1992), "Cardiac Assistance From Skeletal Muscle: A Critical Appraisal of the Various Approaches", British Heart Journal, vol. 68, pp. 333-338.

Ugolini (1986), "Skeletal Muscle for Artificial Heart Drive: Theory and in Vivo Experiments", Biomechanical Cardiac Assist, pp. 193-211.

Reichenbach, et al. (1997), "In Vivo Studies of an Implantable Energy Convertor for Skeletal Muscle Powered Cardiac Assist", ASAIO Journal, vol. 43, pp. M668-M672 (and Abstract).

Geddes, et al. (1991), "Power Capability of Skeletal Muscle to Pump Blood", Trans Am Soc. Artif. Intern Organs, vol. XXXVII, pp. 19-23.

Reichenbach, et al. (1992), "Characterization and Work Optimization of Skeletal Muscle as a VAD Power Source", ASAIO Journal, pp. M359-M363.

Melvin, et al. (1997), "Coupling of Skeletal Muscle to a Prosthesis for Circulatory Support", ASAIO Journal, vol. 43, pp. M434-M441.

One-Page International Search Report for PCT/US2004/18299, mailed Oct. 5, 2004.

Melvin, D.V.; Conkle, D; Roberts, A; Stinson, E; "Cardiac Perforamnce and Myocardial Contractility After Experimental Mechanical Ventricular Assistance", J. Thoracic and Cardiovascular Surgery vol. 65, Nol. 6, Jun. 1973. (pp. 876-881).

Melvin, D.B., "Cardiovascular Surgery: Myocardial Preservation, Cardiorespiratory Support I", American Heart Assoc. Abstract, Circulation Part II, vol. 68, No. 4; Scientific Sessions for Nurses; 37th Ann. Meeting; Nov. 14-17, 1983. (1 Page).

Melvin, D.; Schima, H.; Losert, U.; Wolner, E., "Long-Term Ventricular Wall Actuation: Can and Should it be Systematically Explored?", Artificial Organs, vol. 20, No. 1, 1996. (pp. 63-68).

Melvin, D.B., et al., "A Physical Analog of the Failing Left Ventricle for In Vitro Studies of Mechanical Wall Actuation", Artificial Organs, vol. 20, No. 3, 1996. (pp. 227-239).

Melvin, D.B., et al., "Reduction of Ventricular Wall Tensile Stress by Geometric Remodeling Device", ASAIO Journal (Abstract), vol. 45, No. 2 p. 166, Mar. 17, 1999. (1 page).

Melvin, D.B., "Device-Induced Ventricular Geometric Remodeling: Appraisal of Critical Issues", J. of Cardiac Surgery (Accepted for publication), Presented at the 3rd Symposium of the Soc. of Cardiac Volume Reduction, Apr. 9, 2000 in Osaka, Japan.

Four-page International Search Report mailed Mar. 24, 2004 for PCT/US2003/30302.

Two-page International Search Report mailed Nov. 2, 2004 for PCT/US2004/18277.

Four-page International Search Report mailed Nov. 19, 2004 for PCT/US2004/18298.

One-page International Search Report mailed Feb. 3, 2004 for PCT/US2003/25986.

\* cited by examiner

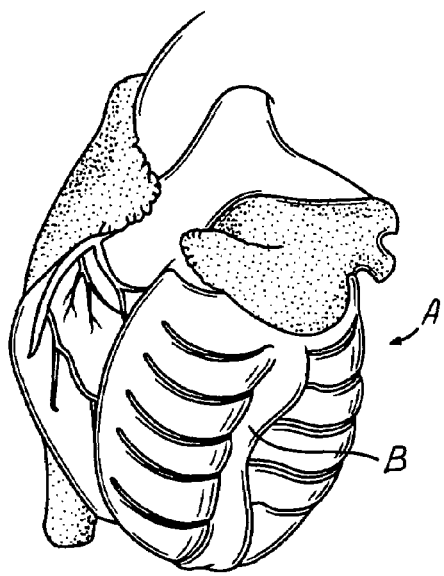

FIG. 1f

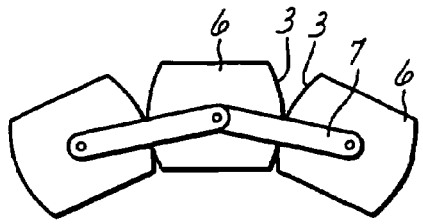

FIG. 2b

| Construction parameters: | | | |
|---|---|---|---|
| Metric (mm, degrees) | base | center | apex |
| block diameter | 9.525 | 9.525 | 9.525 |
| block height excluding peg | 7 | 7 | 7 |
| peg height | 1.5 | 1.5 | 1.5 |
| peg width | 3 | 3 | 3 |
| block thickness | 4.5 | 4.5 | 4.5 |
| tongue and socket angles | 12.761 | -2.169 | 15.081 |
| tongue flare angle | 29.15 | 29.15 | 29.15 |
| | | | |
| Construction parameters: | | | |
| English (inches, degrees) | | | |
| block diameter | 0.375 | 0.375 | 0.375 |
| block height excluding peg | 0.2756 | 0.2756 | 0.2756 |
| peg height | 0.0591 | 0.0591 | 0.0591 |
| peg width | 0.1181 | 0.1181 | 0.1181 |
| block thickness | 0.1772 | 0.1772 | 0.1772 |
| tongue and socket angles | 12.761 | -2.169 | 15.081 |
| tongue flare angle | 29.15 | 29.15 | 29.15 |

8.0864
33.786

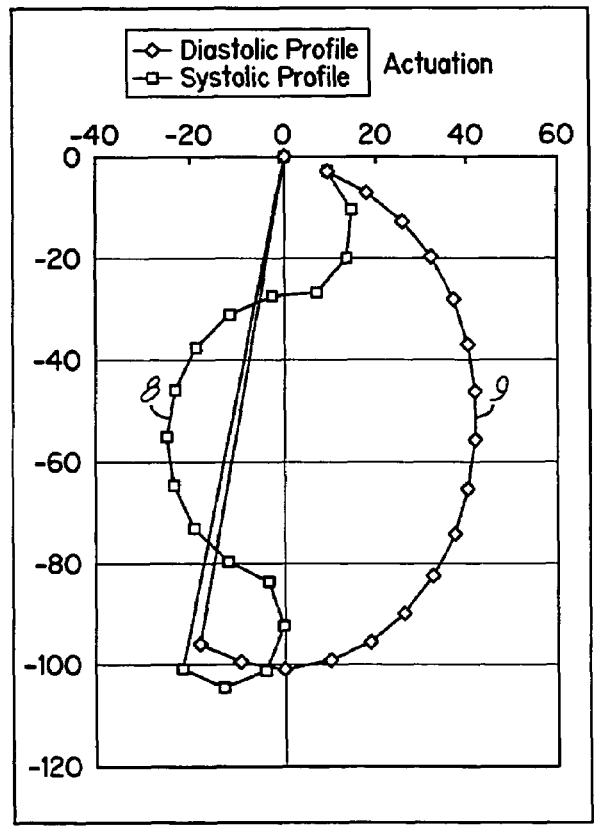

FIG. 3

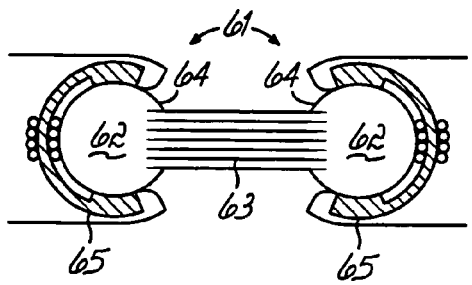
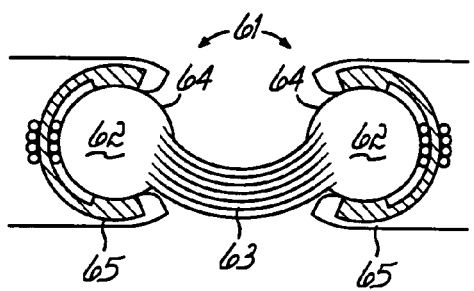
FIG. 13a  FIG. 13b
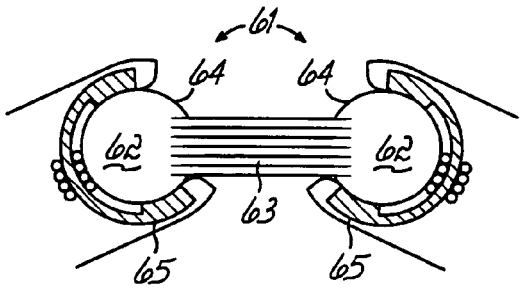
FIG. 13c
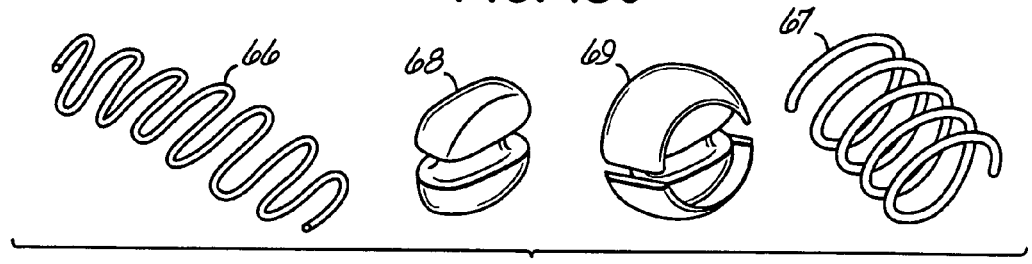
FIG. 14a
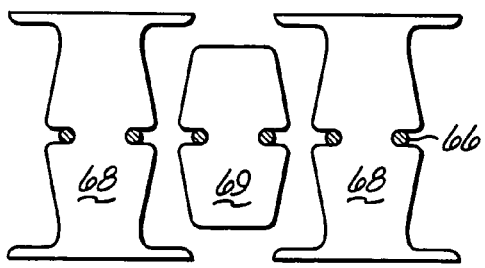
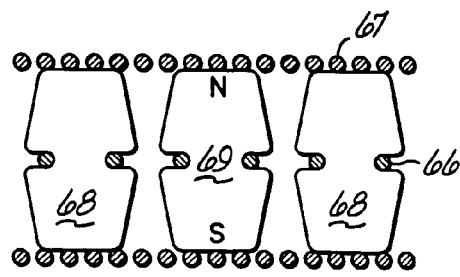
FIG. 14b  FIG. 14c
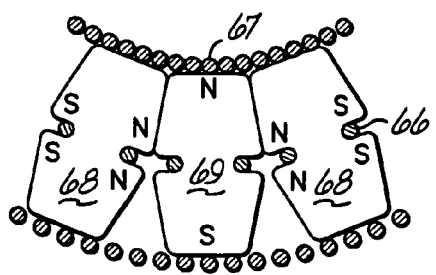
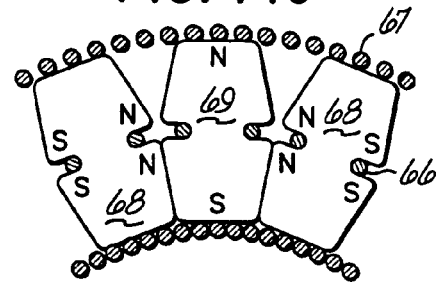
FIG. 14d  FIG. 14e

ACTUATION MECHANISMS FOR A HEART ACTUATION DEVICE

This application is a continuation of PCT/US2004/018277 filed on Jun. 9, 2004, which claims priority of U.S. Provisional Patent Application No. 60/477,077, filed Jun. 9, 2003. The disclosure of each priority application is hereby incorporated by reference herein in its entirety.

FIELD OF THE INVENTION

This invention relates generally to assisting the natural heart in operation and, more specifically, to components to assist in actuating one or more walls of the natural heart.

BACKGROUND OF THE INVENTION

The human circulatory system is critical for survival and systematically provides nutrients and oxygen as well as removing harmful waste products from all parts of the body. The heart is a critical component of the circulatory system in that it provides pumping power. Generally the right side of the heart receives blood from the 'systemic circulation' (all the body except the lungs) and pumps it into the 'pulmonary circulation' (lungs), whereas the left side of the heart receives blood from the lungs and pumps it back into the systemic circulation. Each side comprises an inflow or collecting chamber with a thin muscular wall, its 'atrium' and a thicker, more powerful muscular pumping chamber, its 'ventricle', which alters volume cyclically due to contraction and relaxation of the muscles in its walls. One-way valves are positioned in the passageway between the left and right atrium and the corresponding ventricle, and between each ventricle and the large arteries that conduct blood into the systemic or pulmonary circulation, respectively. Because of this arrangement, each atrium may gently contract, causing blood to flow across the 'atrioventricular' valve into the ventricle, with that valve then closing to prevent return. Similarly, each ventricle may then forcefully contract, causing blood to flow across the outflow valves into the systemic or pulmonary circulation. A physical ailment or condition which compromises the effective muscular contraction in the walls of one or more chambers of the heart can therefore be particularly critical and may result in a condition which must be medically remedied if the person is to long survive.

More specifically, the muscle of the heart may degrade for various reasons to a point where the heart can no longer provide sufficient circulation of blood to maintain the health of a person at an acceptable level. In fact, the heart may degrade to the point of failure and not been be able to sustain life. To address the problem of a failing natural heart, solutions are offered to maintain the circulation. Some of these solutions involve replacing the heart. Some involve assisting it with mechanical devices. Some are directed to maintain operation of the existing heart.

The heart may be removed and replaced with either a mechanical device (a total artificial heart) or a natural heart from another human or an animal (heart transplant). Artificial heart use has been complicated by consequences of blood clots forming on the internal lining. The most serious consequence is a breaking loose of such clots that are then propelled into various parts of the circulation. In the event of such a clot being propelled into the brain, a disabling or fatal stroke may result. While human heart transplantation is limited by rejection, a response of the body's immune system, this may usually be controlled by medications to the degree that half of all recipients survive at least 10 years, generally with acceptable health and function. However a more serious limitation is numbers of available donors. These are usually accidental death victims whose hearts maintain function despite brain death. Currently these are available for less than 1 to 2 percent of potential beneficiaries (about 2000 per year in the United States for over 200,000 people dying of heart failure annually in the same country, for example).

The heart may be assisted by mechanical auxiliary pumps. These are of three general types: counterpulsators, pulsatile assist systems, and nonpulsatile assist systems. Counterpulsators such as intraaortic balloon pump cyclically remove or displace blood from the arterial system in synchrony with the natural heart's beat and, without valves, may perform substantial work for a weakened heart. Pulsatile assist systems (ventricular assist devices) are similar to artificial hearts except that they are used in addition to one or both sides of the heart rather than instead of the heart. They receive blood from either the atrium or ventricle on one side of the circulation and pump it into that side's arterial system, relieving the ventricle of part of its volume load, pressure load, or both. They consist of a blood chamber with at least partial wall flexibility, inflow and outflow valves, and some means, usually pneumatic, hydraulic, or electric, by which the wall may be moved and volume altered to pump blood. Nonpulsatile assist systems are rotary pumps, either centrifugal, axial flow, or a combination, that similarly pump blood in a steady flow from atrium or ventricle into circulatory systems. All of these mechanical pumps have extensive non-living material surfaces that contact blood. The complications of blood clotting with stroke or other serious aftermaths described with artificial hearts also occur with these mechanical auxiliary pumps.

Because of the severe shortage of human donor hearts for transplant, unsolved immunologic problems of animal donor hearts for transplants and prevalence of serious complications of artificial blood-contacting surfaces of both artificial hearts and auxiliary pumps, means of aiding the actuation of the natural heart walls have been attempted. Both skeletal muscle wraps ('cardiomyoplasty') and mechanical compression devices ('mechanical ventricular actuation') have been used. In either approach, the external wall surfaces of the heart are compressed and the heart volume altered, thereby pumping blood out of the chambers. Muscle wraps are limited by available space relative to muscle mass required for power, as well as by intrinsic stiffness that compromises re-filling between beats. Both muscle wraps and mechanical compression devices are limited by inability to effectively restrict volume and pressure delivery to one chamber of the heart. This chamber restriction is important because the two sides of the circulation require far different pressures for acceptable function (usually the systemic pressure is 3 to 5 times as high as is the pulmonary pressure). Compressive patterns of either muscle wraps or mechanical devices may also distort heart valves, which can lead to valve leakage.

Therefore, to be effective and safe, mechanical pumping of a person's existing heart, such as through mechanical compression of the ventricles or some other action thereon, must address these issues and concerns in order to effectively and safely pump blood. Specifically, the weakened ventricle or ventricles must rapidly and passively refill between beats at low physiologic pressures, and the valve function must be physiologically adequately. The blood flow to the heart muscle must not be impaired by the mechanical device. Still further, the left and right ventricular pressure independence must be maintained within the heart.

Internal stabilizing components to complete the three-dimensional control of a chamber's boundaries, which components are suspended through the substance of heart walls from the external (to the heart) actuating mechanism should be a useful adjunct. These provide a means to facilitate the precise control of actuation—determining the prescribed pattern and distribution needed to (1) prevent valvular distortion, (2) avoid myocardial blood flow compromise, (3) provide a type of shape alteration of the actuated chamber at end-actuation which will facilitate passive refilling during shape restoration, and (4) ensure relative independence of pressure in the various chambers.

Specifically, U.S. Pat. No. 5,957,977, which is incorporated herein by reference in its entirety, discloses an actuation system for the natural heart utilizing internal and external support structures. That patents provides an internal and external framework mounted internally and externally with respect to the natural heart, and an actuator device or activator mounted to the framework for providing cyclical forces to deform one or more walls of the heart, such as the left ventricular free wall. The invention of U.S. patent application Ser. No. 09/850,554, which has issued as U.S. Pat. No. 6,592,619, further adds to the art of U.S. Pat. No. 5,957,977 and that patent is also incorporated herein by reference in its entirety. The application specifically sets forth various embodiments of activator or actuator devices, which are suitable for deforming the heart walls and supplementing and/or providing the pumping function for the natural heart. Conceptually, this is a hybrid type of artificial heart in which the blood contacting surface is the recipient's own heart chamber linings and the only function replaced is that which is deficient, and ultimately absent, in the native heart: power to move those blood-friendly heart walls. The function that has most frustrated research into mechanical circulatory support, safe blood contact, is simply circumvented.

While the actuation systems of those patents provide a desirable actuation of the natural heart, it is further desirable to improve upon durability and safety of those actuation systems. It is particularly desirable to actuate the ventricular in ways that minimize risk of either mechanical or biologic malfunction over an extremely large number of cycles and to do so in a fashion that optimizes induced function of each of the two anatomically differing ventricles. The natural heart beats approximately 1 billion times ($10^9$ cycles) over 25 years, a reasonably desirable endurance for middle-aged recipients of such devices.

Several obstacles to reaching that goal have been observed in earlier and in conventional implanted medical devices, both for cardiovascular and other purpose.

First, devices in which action of mechanical members requires a residual air chamber (for example, many of the electrical ventricular assist devices) have only succeeded, clinically or experimentally, by having either an external vent or a frequently refillable compliance chamber.

Second, prolonged cyclic stress on flexing polymer membranes has often been complicated by either membrane mechanical failure or mineralization with unacceptable stiffening. Yet such membranes, often under substantial cyclic stress are needed if moving mechanical parts are to be shielded from either affecting or being effected by tissue and tissue fluid.

Third, if mechanical members are, conversely, to contact tissue, crevasses and spaces between those moving members which do not allow and promote free flow of bathing tissue fluid are followed by several complications of such stasis. Infection is particularly common due to restricted access to such areas by the immune system. Interfaces between metals under such conditions are susceptible to fretting corrosions. With or without fluid stasis, interfaces between two or more dissimilar metals may generate galvanic currents with electrolytic corrosion of one or both metals. Further, irregular moving surfaces and edges may mechanically damage surrounding tissue or encourage immobilizing scar tissue that inhibits function.

The embodiments described herein are based on avoidance of these complications and so facilitate prolonged clinical durability with minimization of biologic and mechanical failure risk over many years of safe, effective actuation of heart walls that have severely weakened or even totally ceased natural movement.

BRIEF DESCRIPTION OF THE DRAWINGS

FIGS. 1a-1f. Articulating mechanisms between discrete links on the surface of the heart by which heart wall bending may be induced. FIGS. 1d-f illustrate one embodiment of a platform for utilizing the actuators disclosed herein.

FIGS. 2a-2b. Restraining mechanisms to maintain proximity of articulating discrete links FIG. 3. A computational model to guide articulating link actuator design, which relates heart chamber volume change to patterns of induced curvature in the actuator, with regional curvature in turn determined by interlink angulation limits.

FIG. 13a-13c. Elastically bending solenoid block driving mechanism including flexible dumbbell-shaped permanent magnets FIG. 14a-14e. Elastically bending solenoid block driving mechanisms in which rigid magnetic members, both permanent and electromagnetic, articulate constrained by helical or serpentine wire springs.

DETAILED DESCRIPTION

Figure 1A:
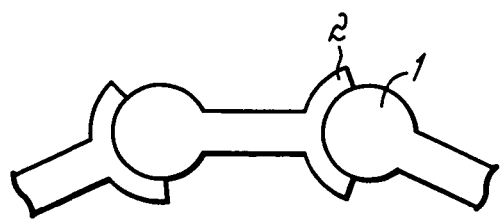
Figure 1B:
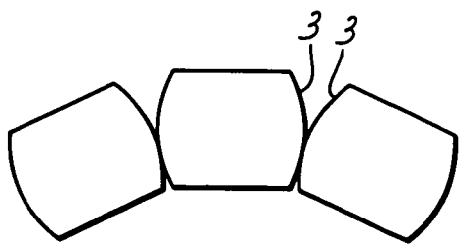
Figure 1C:
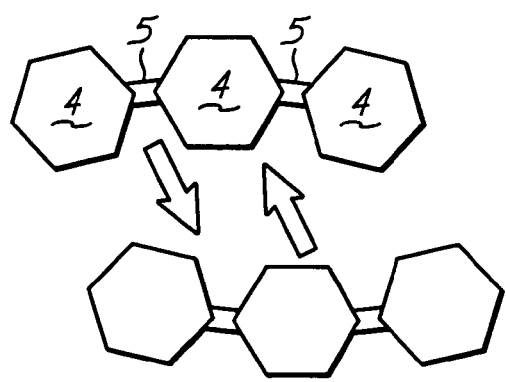
Figure 1D:
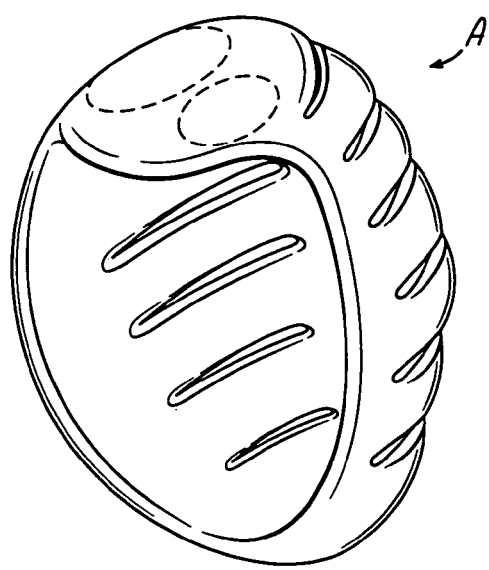
Figure 1E:
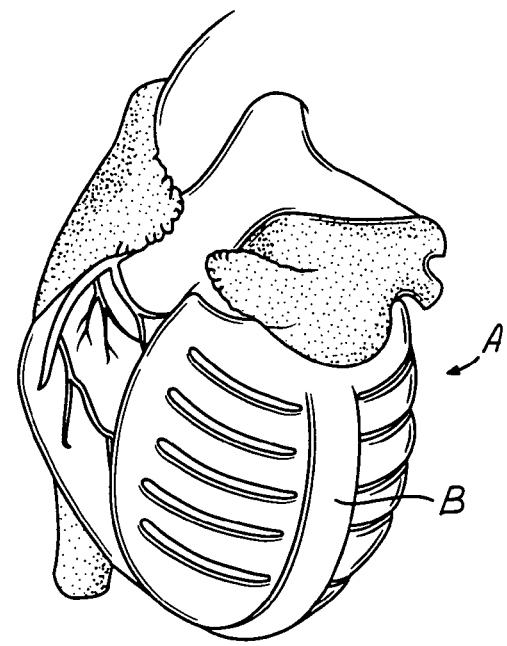

Part List
1. ball or cylinder for a sliding rotary articulation
2. socket for a sliding rotary articulation
3. convex rolling surface
4. rigid element for a flexing linkage
5. flexible element for a flexing linkage
6. links
7. tension member holding rolling links in position
8. profile of an articulating link actuator in full actuation
9. profile of an articulating link actuator in full relaxation
10. rolling surface adjacent tongue component of a tongue-in-socket articulation
11. rolling surface adjacent socket component of a tongue-in-socket articulation
12. tongue component
13. socket component
14. depth of socket
15. length of tongue
16. arc of the mouth of socket
17. arc of base of tongue
18. margin of socket
19. base of tongue
20. base diameter of tongue
21. flare angle of tongue
22. impacting projection
23. impacted depression
24. pin
25. hook
26. basal region
27. central region
28. apical region
29. basal end
30. apical end
31. angle between basal blocks at diastolic limit
32. angle between basal blocks at systolic limit
33. radius of curvature of central section at diastolic limit
34. radius of curvature of central section at systolic limit
35. block 4
36. block 3
37. block 5
38. block 2
39. block 6
40. block 1
41. block 7
42. block 8
43. block 9
44. block 10
45. block 11
46. block 12
47. block 13
48. block 14
49. block 15
50. eccentric tether
51. flexurally elastic heart jacket
52. metal articulating block or link
53. split cylindrical bearing
54. helical tension springs incorporated in heart jacket
55. channels for tethers
56. dumbbell-shaped permanent magnet-containing link
57. double socketed solenoid link
58. head of permanent magnet containing link
59. waist of permanent magnet containing link
60. housing of permanent magnet and solenoid articulating links
61. flexible electromagnetic links
62. permanent magnets in flexible links
63. spring elements in magnetic flexible links
64. rigid heads of flexible magnetic links
65. solenoid housing sockets
66. serpentine wire spring
67. helical wire spring
68. solenoid links configured for spring-mounted embodiment
69. permanent magnet links configured for spring-mounted embodiment
70. heart chamber wall
71. traversing tether
72. flexible compressive sheath
73. anchoring structure
74. traversed section of heart jacket
75. entering and exiting points
76. floating blocks
77. spring elements separating floating blocks
78. right ventricle
79. interventricular septum
80. left ventricle
81. innermost of a set of concentric rings
82. second of a set of concentric rings
83. third of a set of concentric rings
84. fourth of a set of concentric rings
85. central axis of a set of rings
86. radial axes through rings
87. solenoids in rings
88. compression springs between rings
89. telescoping axial brace
90. central core of axial brace
91. first of two orthogonally positioned tethers
92. second of two orthogonally positioned tethers
93. left atrium 94. right atrium
95. aorta
96. pulmonary artery
97. transverse train of articulating blocs configured for left ventricular actuation
98. junctional links of train
99. flexible shafts for rotary power delivery
100. anterior segment of articulating link left ventricular actuator
101. posterior segment for articulating link left ventricular actuator
102. projections on articulating links
103. tether passing through projections on articulating links
104. concentric rings of a right ventricular actuator This application discloses actuators that are used with an overall actuation system to be coupled to a natural heart to assist in the operation of the natural heart. For example, referring to FIGS. 1d, 1e and 1f, the actuators disclosed herein may be utilized with a Jacket that is placed over the heart. They might be incorporated along the Jacket as indicated by B as shown in FIG. 1e to deform the heart, as shown in FIG. 1f. Further disclosure a suitable Jacket or cushion structures for utilizing actuators disclosed herein are set forth in U.S. patent application Ser. No. 10/677,877 filed Sep. 22, 2003, and entitled "Basal Mounting Cushion Frame Component to Facilitate Extrinsic Hart Wall Actuation," and PCT patent application Ser. No. PCT/US04/18277 filed on Jun. 9, 2004, entitled "Deforming Jacket for a Heart Actuation Device." These two applications are incorporated herein by reference in their entireties.

Such applications disclose one type of framework for utilizing the actuators disclosed herein and are not exclusive. Therefore, the actuators disclosed herein might be utilized in other ways for actuating a natural heart to assist in its actuation.

Actuators, which Work Primarily by Regional Wall Bending

The jacket may be fitted with, or may partially incorporate, one or more actuating units whose action, at least in part, is the induction of forceful bending of one or more cardiac walls regionally in order to alter chamber volume. These differ as to (I) geometric organization of the actuating unit or units, (II) mechanism of actuation, and (III) relationship to wall-protecting components.

I. Non-limiting examples of geometric organization of wall-bending actuators are linear (fingers attached at least at one or both ends, with components arranged in one or more separate curvilinear rows), arachnid (structures in which multiple such curvilinear structures are combined in a branching shape) and grid (a continuous or a net/grid surface).

During activation of any of these, the mechanism's shape is cyclically altered.

A. Examples of linear bending-actuator organization include
1. a single bending member, whether operating by multiple points of articulation between rigid parts, material flexion oriented parallel with the long axis of the left ventricle of the heart, approximately midway between the posterior and anterior margin of the left ventricular free wall and extending from a basal end near the atrioventricular groove to an apical end near the apical interventricular groove.
2. An actuator system with multiple, approximately members extending transversely across a left ventricular jacket, each member having anterior, central, and posterior regions.

B. An example of arachnid bending-actuator organization is a starfish-shaped bending tethered hydraulic-tube actuator of the type taught in U.S. Pat. No. 5,957,977
C. An example of grid could be a combination of the two linear examples given above in which the vertical limb or limbs intersects and is fixed to each of the transverse limbs at points of crossing.

Figure 2A:
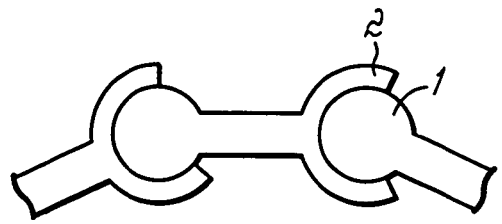

II. The mechanism of actuation by which each of the devices described below forces bending deformation of a heart wall is based on segmental bending. This means that the angulation between adjacent links of a curvilinear assembly of multiple links is induced to change, for example by solenoid activation, by traction on a tether in a compression sheath, or by rotation of a flexible shaft. These actuators are alternatives to the side-tethered hydraulic tubes of various configurations taught more explicitly by U.S. Pat. No. 5,957,977 and have a similar end result. That end result is conversion of another type of energy to cyclic production of a prescribed bending deformation with prescribed bending moments created, heart wall deformed, and heart chamber volume reduced with a concomitant increase in chamber pressure, the level of pressure increase determined by outflow impedance. For the three mechanisms given as examples, the input work is electrical energy ($\Sigma W=\int[E*I]$), linear mechanical displacement ($\Sigma W=\int[F*v]$), and mechanical rotation ($\Sigma W=\int[T*\omega']$), respectively, while the previously patented hydraulic tubes' energetics and the heart's output pumping work are both described as hydraulic pressured flow ($\Sigma W=\int[P*f]$). [W=work, E=EMF, I=current, F=Force, v=velocity, P=Pressure, f=flow, =T=Torque, and $\omega'$=angular velocity] These angulating link actuators are applicable to any chamber; and is the type of actuator presently preferred for left ventricle. It should be best understood by considering (1) the basic structure, which holds the links together and imposes limits on curvature or angulation between links, and then (2) considering various means by which cyclic deformation and restoration may be mechanically imposed.
1. The 'basic structure' of a mechanically driven angulating link actuator includes (a) how the links interface with, and move relative to, each other (b) what holds the links together (c) what imposes limits on curvature or angulation between links and (d) whether deformation is elastic, and if so, to what degree. It will be understood that although examples of specific combinations of these are given and illustrated, any combination of any of the types of interface described may be used with any of the means of curve limitation described, and with any of the means of proximity maintenance described, and so on.
   a. Interface between links: sliding articulation, rolling articulation, and/or flexing of one or more connecting members.
      i. A non-limiting example of sliding articulation between links is the ball-in-socket or cylinder-in-socket, a section of which is illustrated in FIG. 1a. The ball or cylinder [1] slides in a mating socket [2] allowing the links to angulate relative to each other. Generally, materials for the interfacing and sliding surfaces will be chosen from the combinations which have performed satisfactorily clinically in artificial joints—combinations of stainless steel and ultrahigh molecular weight polyethylene, cobalt-chromium alloy and hardened ceramics, for two examples.
      ii. A non-limiting example of rolling articulation is illustrated in FIG. 1b. Similar materials to those used in the prior paragraph would be acceptable, with compression resistance being of particular importance. One or both of the facing surfaces [3] that roll on each other must be convexly curved in at least one plane. However, rolling surfaces of similar metals may also be practical, since tissue fluid exchange should be sufficient to avoid fretting corrosion.

iii. A non-limiting example of elastically flexing articulation is that diagrammed in FIG. 1c. Generally, rigid elements [4] are joined by flexing elements [5]. Among possible materials for flexing elements [5] are coiled or serpentine metal wire springs, thin metal strips, glass and epoxy or carbon fiber and epoxy composites, polyester fiber and elastomer (e.g. polyurethane or silicone rubber) composites. Matching materials and load for predictable and acceptable rates of fatigue endurance is critical.

b. Means of maintaining proximity are physical interlocking and interconnecting flexible members. These two means may be combined.

i. Physical interlocking is illustrated by the non-limiting examples of FIGS. 2. 2a is a sliding articulation in which the articulating surface of the member on the right (a socket [2]) extends more than 180 degrees about the articulating surface of the member on the left (a ball or cylinder [1]), intrinsically maintaining proximity. 2b is an example of links [6] with rolling articulation on each other, held together by at least one tension member [7], pinned to the two links at the centerline of curvature for the rolling contact surface [3] of each.

ii. Interconnecting flexible members may hold links together, either as illustrated by the example shown above in FIG. 2c, in which the flexion member [5] is the primary or sole means of articulation, or as illustrated below by the tensed spring of FIG. 14, a flexion member may serve to maintain apposition for a rolling or sliding articulation. In either of these variations, the flexing member or members may also serve as a means of imposing and controlling the degree of flexural elasticity or stiffness on deformation.

c. Means of limiting curvature and angulation. 'Curvature' herein is used in the usual mechanical engineering sense of the inverse of the radius of curvature with units that are the inverse of length (e.g., $mm^{-1}$, $inches^{-1}$, etc.). Thus the more curved the greater the absolute value of curvature, with the sign (+ or −) indicating the direction of curvature. The following two mechanisms are believed particularly suitable for direct incorporation in the articulating link actuator, however. The principle distinctions from angle-limiting features of articulating mechanisms in non-medical application (door hinges, cutting shears, and so forth) are design characteristics to minimize (1) opportunities for stasis of the tissue fluid which will inevitably bathe and surround the components (counter principally by designing recesses with openings at least as wide as deeper regions and providing frequent agitation of fluid at recess openings) (2) risk of entrapment of tissue (countered principally by avoiding or minimizing opening and closing of fissures that face tissue, as well as rounded and beveling of edges). Two non-limiting examples are the tongue-in-socket and the impacting projection mechanism. Of these two preferred mechanisms, the tongue-in-socket imposes limits of angulation in both directions, while a single impacting projection only limits in one direction. The two mechanisms may be determined to be optimally used together in different parts of a single device, each in a region or regions for which its advantages are most important.

Figure 4:
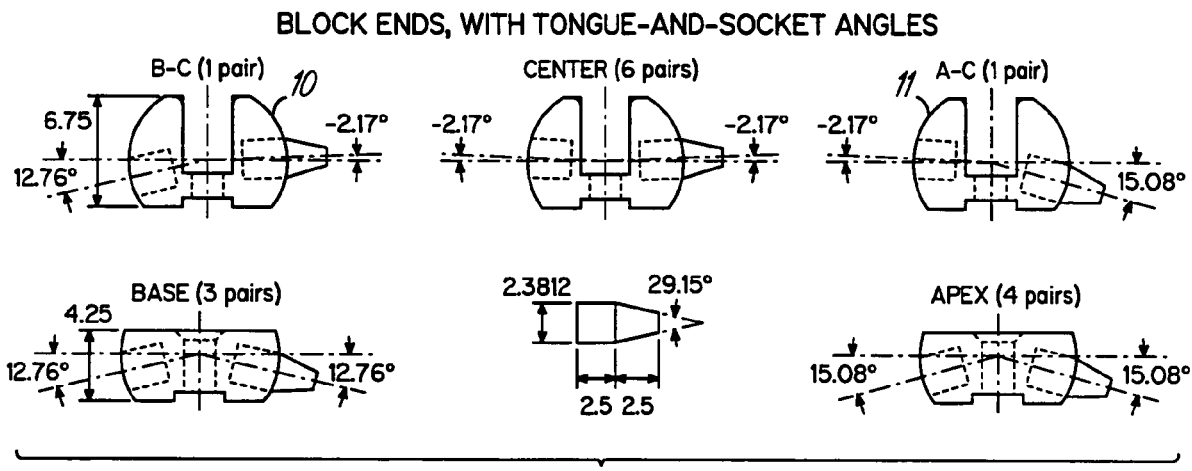
FIG. 4. Links designed according to the prescriptions of the model shown in figure 3.
Figure 5:
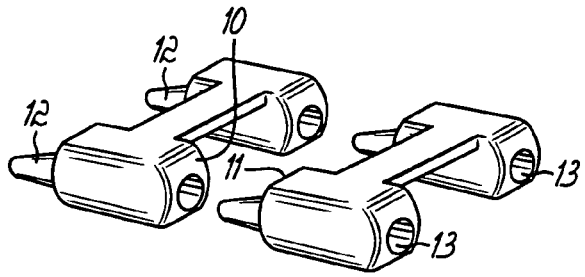
FIG. 5. Perspective view of articulating links of a preferred embodiment, in which inter-link angle limitation is determined by the angles and dimension of a tongue-in-socket junction FIG. 6a-6c. Sectional drawings of tongue-in-socket junctions in maximum, midrange, and minimum angulations.
Figure 6A:
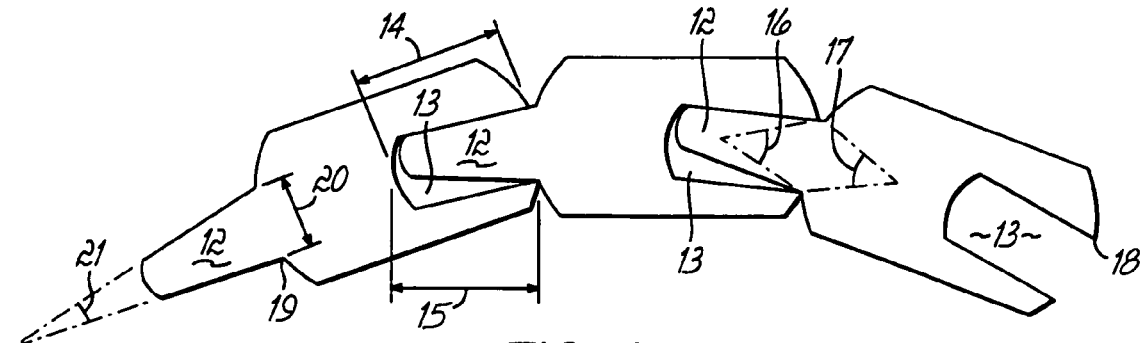
Figure 6B:
Figure 6C:
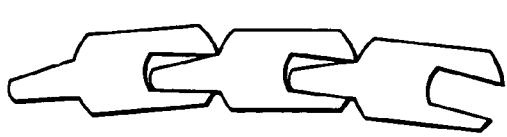

A preferred means of design is illustrated in figures FIG. 3 and FIG. 4, specifically for the tongue-in-socket but equally applicable to the impacting projection or other mechanisms. The limit or limits of curvature (maximum limit, minimum limit, or both with minimum being a negative number if curvature changes from concave to convex in a given direction) are prescribed by plotting desired geometry in full activation [8] and again in full relaxation [9], as in FIG. 3, and used to determine specifications as shown in the example of FIG. 4.

i. Tongue-in-socket mechanism. A non-limiting example is illustrated in FIG. 4 (CAD drawing), FIG. 5 (perspective), and FIG. 6 a, b, and c (sections). In this example, the inter-link interface is by rolling articulation between two facing curved surfaces [10,11], generally arcs of circles in the plane of angulation. A tongue [12], generally shaped either as a truncated cone (as shown) or as a projection having a similar configuration in long section but having a different (for example, rectangular) configuration in cross section, extends from one of the curved surfaces into a socket [13], generally cylindrical. The depth [14] of the socket must exceed the length [15] of the tongue. The arc [16] subtended by the mouth of the socket must at least equal the arc subtended by the base [17] of the tongue; any excess should be relatively small to minimize slippage. The margin [18] of the socket and the base [19] of the tongue may be radiused to lessen stress concentration. Angulation between the two links of FIG. 5 and of FIG. 6, and thus curvature of the larger mechanism of which the links are a part, is constrained between a maximum and a minimum. For this discussion, angulation is considered the angle between the tangent lines of each of the blocks with the surface of the heart-whether the blocks directly contact the heart or are separated from it by a protective barrier.

Figure 7A:
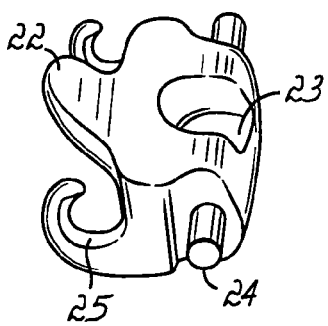
FIGS. 7a-7c. A nonlimiting example of an impacting-projection design for controlling interlink angulation in a perspective a single link and of two mating links in states of relaxation and of maximum angulation.
Figure 7B:
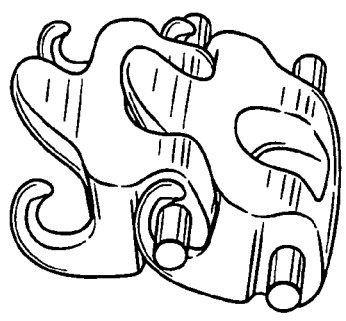
Figure 7C:
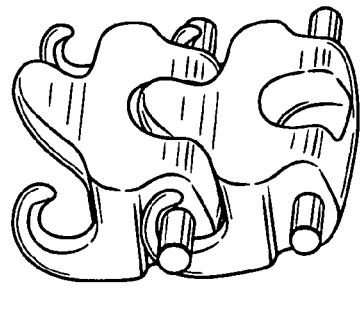

It will be apparent that these minimal and maximal angulation values are a function of several variables: the base diameter of the tongue [20], the flare angle [21] of the tongue (as well as the angle between opposite walls of the socket if not parallel as shown), and the angle between the center of curvature of each link's articulating surface and the midline of the associated socket or tongue.

ii. Impacting projection mechanism. A nonlimiting example of this is the configuration shown schematically in FIG. 7. A perspective view shows a single link in 7a. 7b is a diagram of two links in a relaxed position. In this configuration, projection [22] is over depression [23] but not impacting the base of the depression. With application of a bending moment to the structure in 19c, the projection [22] impacts the base of depression [23] to halt relative rotation. In this example, articulation and relative fixation of the links is provided by the sliding interface between pin [24] and hook [25]. Smooth, rounded contours of the impacting surfaces, as well as dimensions which preferably assure that projection [22] will never totally leave depression [23] in the presence of forces expected after implantation, may be reasonably expected to reduce or eliminate likelihood of tissue entrapment and to facilitate, with continued motion, biologic response that makes a smooth fibrous tissue encapsulation likely.

Pin [24], hook [25], or both, may be surface by a material that differs from the body of the link to achieve high compression strength and/or improved friction and wear characteristics. A non-limiting example is a hook [25] surfaced on its articulating surfaced with a hard ceramic to facilitate interaction with a machined metal pin [24]. In general, material combinations that have functioned well in clinical artificial joint applications in regard to durability and favorable biologic response would be expected to function well in this application.

d. Elasticity in deformation has potential advantage storing energy during one part of the cycle so as to not require extrinsic energy during another part of the cycle. For example, it would allow a modestly increased energy input during imposition of cardiac systole to permit omission of extrinsic energy input during the less-demanding shape restoration of cardiac diastole. This may be particularly advantageous, for example, if energy is delivered by a flexible shaft, where design constraints of a unidirectional shaft—activated intermittently—may be considerably simpler than those for a bi-directional shaft. It may be similarly advantageous if energy is delivered by traction tether, where displacement in the opposite direction is problematic.

2. Means of deformation. Deformation of an assembly of articulating links with strictly limited angulation at each inter-link interface, by the means described above or by other means may be imposed by simultaneously restraining both ends from moving away from a resisting distributed load and inducing rotation, in the plane of bending, of at least one link, and preferably at least two.

Figure 8:
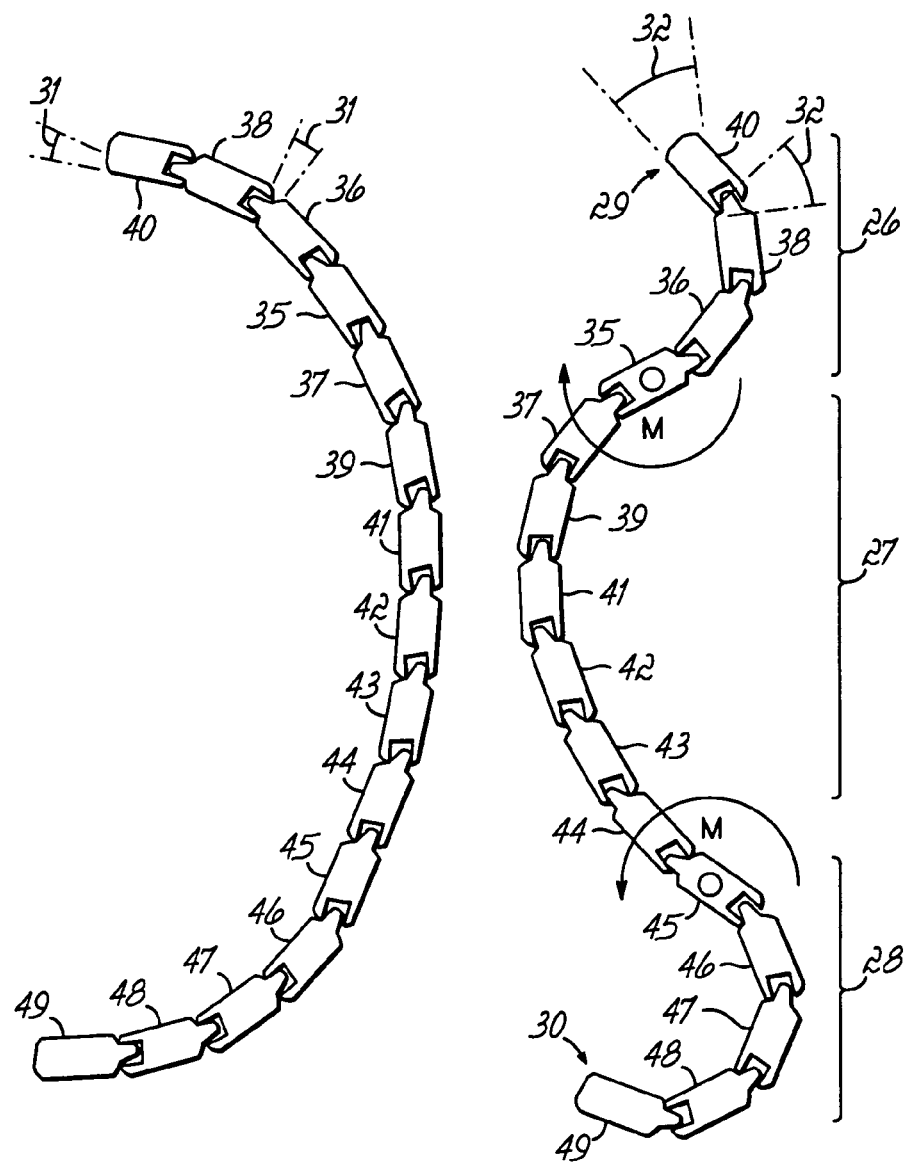
FIG. 8. A preferred means of inducing deformation in an articulating-link actuator by applying torsion to at least one link with curvature in all regions being secondary effects.

This restraint is achieved by fixing at least the ends to a jacket, described and filed for patent protection separately, which is in turn anchored to the heart. Rotation of at least one link may be achieved either (i) directly by applying torsion to at least one link, with curvature of all regions being a secondary effect and (ii) indirectly by primary imposition of curvature to one or more regions of the assembly by any means so that link rotation at the ends of that region is a secondary effect and induced curvature of the remaining regions (between the region on which curvature change has been imposed and the two ends) a tertiary effect. These are schematically presented in FIG. 8 and in FIG. 9, respectively. FIG. 8 includes the preferred method of primarily imposing curvature, imposing torsion on one or more links. Positional torsion may be achieved by a suitable rotating mechanism. For example, some suitable mechanisms to couple to one or more links for rotation are set forth in PCT application filed on Jun. 9, 2004, entitled "Power System for a Heart Actuation Device," which application is incorporated herein by reference.

The sequential events following induced rotation of one or more links are summarized in the following few paragraphs. Following that summary, two means of inducing rotation (referenced above as "i" and "ii") will be described separately.

Interface geometry at each articulation of links is designed to set minimum and maximum angulation limits for the interfaces in that articulation, for example, by the means described above in sections B1$ci$ and B1$cii$. To illustrate the sequence of action, consider the non-limiting example of a single, longitudinal, train of articulating links described above (IA). Such a train may have three regions ('basal' [26], 'central' [27] and 'apical' [28] in the embodiment of FIG. 8) with two terminal fixation (in the embodiment of the previous paragraph, at the basal end [29] of the basal region and at the apical end [30] of the apical region), and two junctional links joining the terminal regions to the central region. For example, a train might have 3, 6, and 4 links in its basal, central, and apical regions, respectively which with the two junctional links yield a total of 15 links. Behavior is determined by the geometry of the links and of their interfaces.

Figure 9:
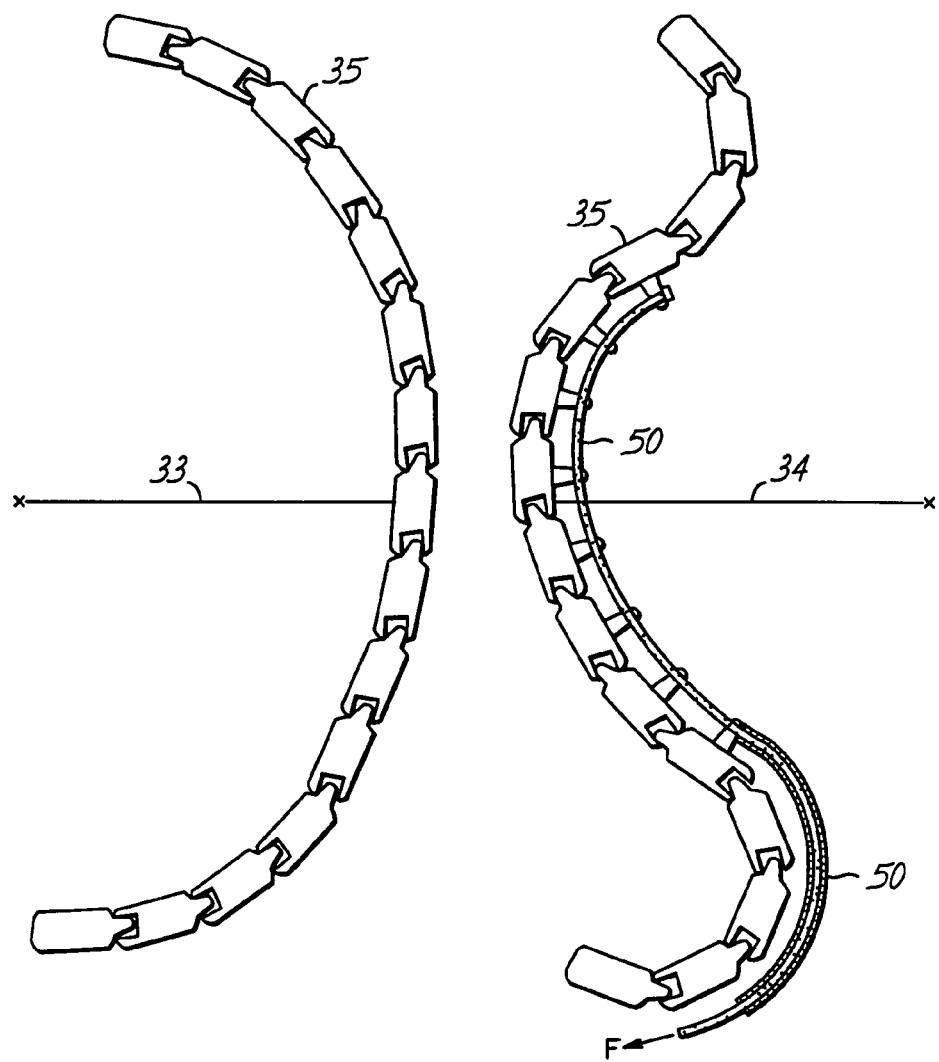
FIG. 9. An alternative means of inducing deformation in an articulating-link actuator by applying traction to one or more eccentric tethers.

For each region permissible motion may be defined by interlink angle (illustrated below for the basal section of the assembly of FIG. 8) or by magnitude and direction of the radius of curvature (illustrated before for the central section of the assembly of FIG. 9} In this example (having 15 total links, 14 total interfaces) the three basal region link interfaces (two basal-to-basal, and one basal-to-junctional) may be designed to allow angulation in that region to vary from about 12 degrees at end diastole [31] to near 40 degrees at end-systole [32], both concave toward the heart. The arc inscribed by this region would be the sum of the four interface angles. Arc radius $\approx \Sigma d/\Sigma \theta$, where 'd' is the distance between points of linkage articulation, slightly less than twice the link's radius, and '$\theta$' are the individual interlink angles. So, with a 9 mm inter-articulation distance, the basal region of the train of linkages would cyclically change from a relatively tight, 120 degree arc of $\approx (3*9)/(3*40*(\pi/180) \approx 12.9$ mm radius at end-systole to a much more open 36 degree curve of about 43 mm radius at end-diastole.

Similarly, the 7 junctions of the central section impose angulation limits that allow the region to cycle from a curve of about 50 mm radius [33] concave to the heart at end-diastole to one of about 30 mm radius convex [34] to the heart at end-systole.

Design, and thus prescribed limits, for apical region are similar but not necessarily identical to the basal region. In the example above, the 4 junctions of the apical region might be conformed to allow the region to cycle from about 40 mm radius of curvature at end-diastole to about 11 mm radius of curvature at end-systole.

The sum of all positive (defined as becoming more concave toward the heart) and negative (defined as becoming more convex toward the heart) angle excursions from end-diastolic to end-systolic configuration is preferably relatively small, i.e., <~15 degrees or ~0.25 radian. This sum may be prescribed by determination of the angulation range permissibility of each of the individual interlink interfaces, and should be the desired relative diastolic-to-systolic angular deformation, if any, of the jacket portions adjacent the two extremities of the train of links—e.g., basal margin relative to apical margin.

Even though interlink interface angles within single regions were identical in the examples given, the angles, link lengths, and thus local radius, may actually vary within a region if that is believed desirable and the components designed to achieve that and render a region that is not a circular arc.

If, in the example above, assuming relative angular fixation of each end of the assemblies, either or both of the junctional links in FIG. 8 are forced to rotate in the directions indicated by the applied moments in FIG. 9, then the configuration of links, in the presence of a resisting distributed force from the left as drawn, will progress toward the shape diagramed in FIG. 9.

To illustrate: if, with such a distributed load from the left, and fixation of both terminations preventing horizontal movement, a clockwise torque is applied to the fourth block [35], then it will respond by rotating clockwise. The angle at the interface between the third block [36] and the fourth block [35] will become more concave to the heart and the interface between the fourth block [35] and the fifth block [37] less concave and then convex until limits are reached (not necessarily simultaneously). Then blocks 3 [36] and 5 [37] will also rotate until the 2-3 (parts [38] and [36]) and 5-6 interface ([parts [37] and [39]) angle limits are reached, then the 1-2 and 6-7. (other block part designations are block 1, [40] and block 7 through 15 designated as parts [41] through [49], respectively]).

With no more rotation permitted by the constraints in the basal region, the part [41-42], part [42-43], [43-44] and [44-45] interface angles will steadily become less concave and then convex toward the left (i.e., the side facing the heart wall, the resistance of which is exerting the distributed load). By this point, with the ends of the assembly being relatively fixed rotationally (i.e., slight rotation only against stiff elastic mountings), the [46-47], [47-48], and [48-49] interface angles will have become of necessity progressively more concave toward the heart in order that minimal change in the angulation of the two ends relative to one another occur.

It will be apparent that simultaneous application of torque to both, rather than one, junctional link (i.e., to block 11 [45] counterclockwise as well as block 4 [35] clockwise), the same deformation will occur. An embodiment permitting this dual-site torque delivery is preferred, since there is a major reduction in greatest bending moment on the structure, and thus the greatest stress on components.

Included in the mechanisms for inducing such link rotation are the following:

i. Direct application of torque to one or more links, for example at the points (links 4 [35] and 11 [45] in FIGS. 8 and 9) may be achieved by, as nonlimiting examples:
   a. Connection of a flexible shaft to one, or preferably both, sides of the link.
   b. A solenoid or other magnetic coupling directly inducing rotation.
   c. The required driving motion—relative rotation of the junction links toward each other—imposed by any other method familiar to the field of mechanical design applied directly to one or both of the two junctional links
ii. Induction of curvature change in at least one region of the train of links (i.e., two or more sequential links) by necessity induces relative rotation of the two links at the ends of that region as a secondary effect. Two means of doing this are by (a) traction on one or more eccentric tethers and (b) a solenoid driven system.
   a. Such curvature may be induced by traction on one or more eccentric tethers [50] as shown diagrammatically in FIG. 9. Tethers may be any flexible tension member such as a cable—whether polymer or metal—or a chain. These pass through channels to one side of the line of flexion, rolling articulation, or sliding articulation. On each interface between links, a moment is produced in the structure equal to the combined tension in tethers and the perpendicular distance between the articulation or flexion point and the tether's central axis.

Figure 10:
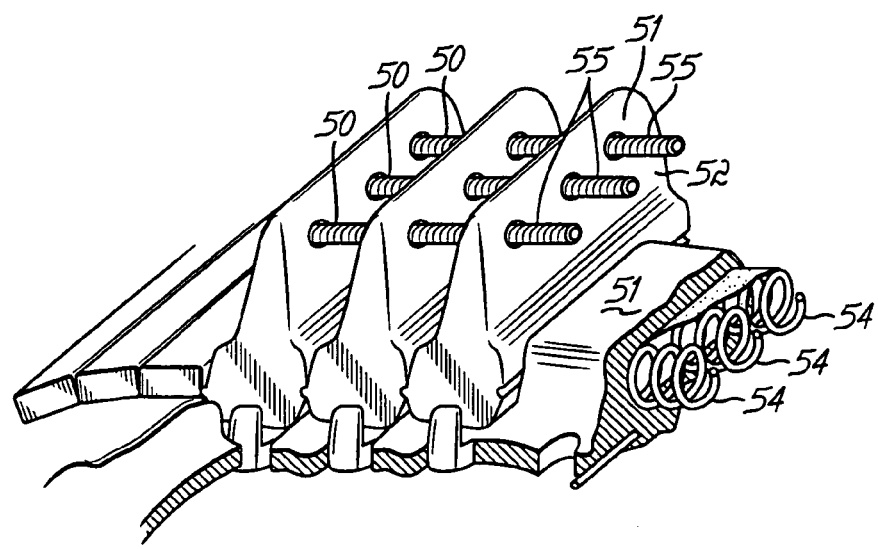
FIG. 10. One specific combination of specific means of apposition maintenance, of interlink angulation control, and of powered curvature induction.
Figure 11:
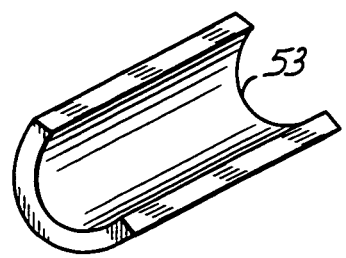
FIG. 11. A split-cylinder configuration for sliding tether bearings for use in an articulating link heart-wall actuator powered by cyclic traction by one or more tethers FIG. 12. Solenoid block driving mechanism for an articulating link actuator in a relaxed and in an activated state.

In an embodiment of this mechanism illustrated in FIG. 10, several of the features noted above are combined. Adjacent articulating links are held in apposition to each other by means of both being mounted on, and/or partially incorporated in, a portion of a flexurally elastic heart jacket [51] which includes helical tension springs [54], as well as tongue-and-socket or tongue-and-groove or other obvious interlocking variations to prevent shear displacement and control curvature as described above. Multiple cable (for example, of metal or of polymer strands) tethers [50] pass in channels [55] in metal blocks [52]. To avoid metal-to-metal sliding in the case of metal tether cables and metal links, and thus the risk of either fretting corrosion (with similar metals) or galvanic erosion (with dissimilar metals), bearings of a hard non-metallic material such as a ceramic, generally cylindrical, are placed as inserts [53] such as shown in FIG. 11, in the tether channels surrounding the tethers. Because of its very hard surface and documented wear resistance in artificial heart valve applications, pyrolytic carbon is the preferred material for bearings. Either cobalt chromium alloy or cp titanium is preferred for the cable and link bodies because of freedom from galvanic currents that have been reported with pyrolytic carbon and stainless steel interfaces. To facilitate the sputter-deposition of pyrolytic carbon on graphite base material which is commonly used in manufacture, two half-cylinders rather than one whole cylinder may be used for each bearing, as shown in FIG. 11.

There are several variations possible for the traction-driven articulating link actuator from the basic structure diagrammed in FIG. 9.

In one variation, a tether or tethers in a second path is configured such that a shortening force in that tether or tethers effects a return of at least one region of the assembly toward its original or resting state.

In another variation, actuators may have more than one train of articulating links with the various trains parallel to each other, at any angle to each other, with trains either intersecting or not intersecting each other. In the event that two or more trains of articulating links intersect, one or more links may be a member of two or more trains, with tether channels configures so as not to interfere with each other.

Figure 12:
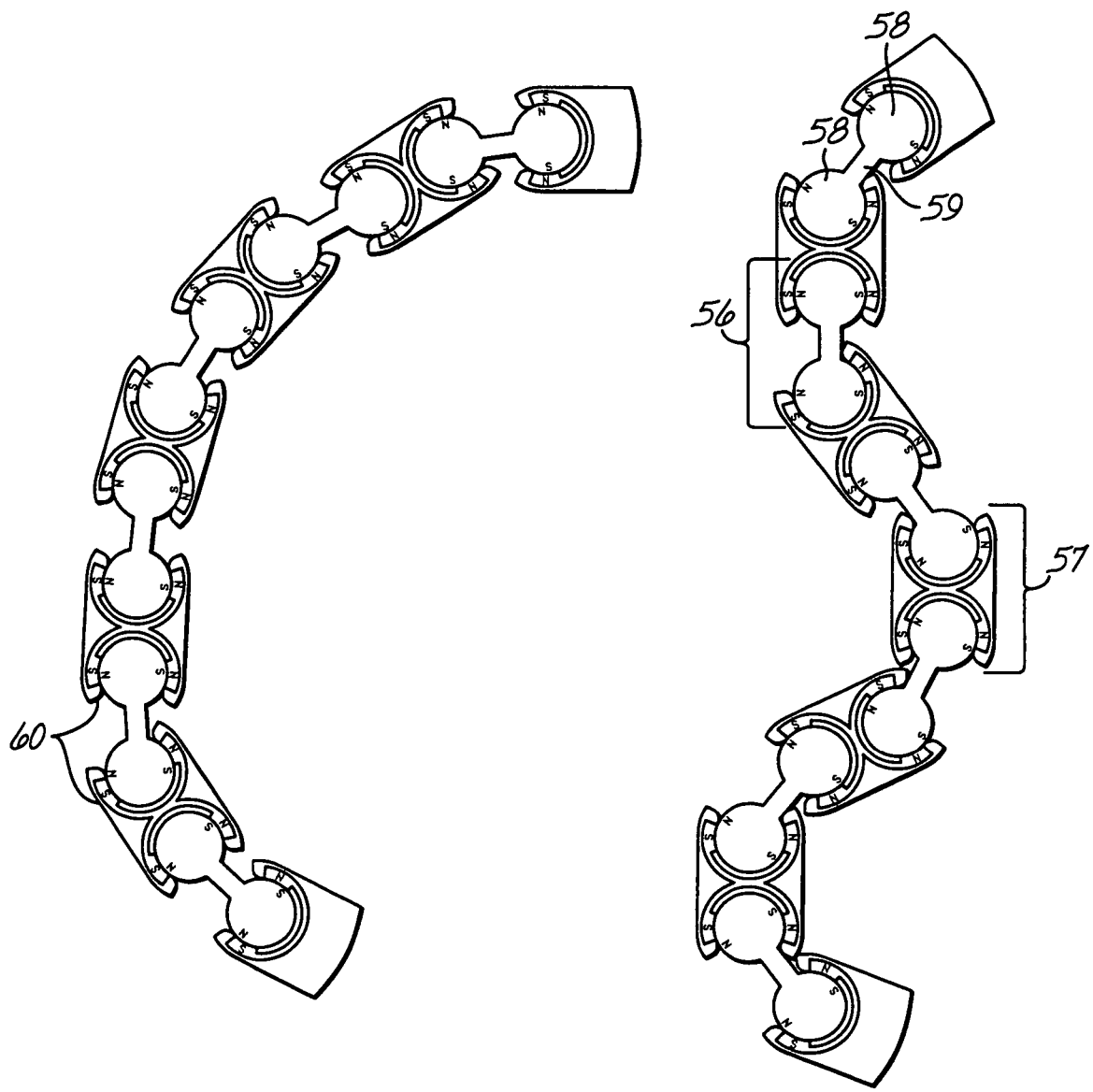
Figure 24A:
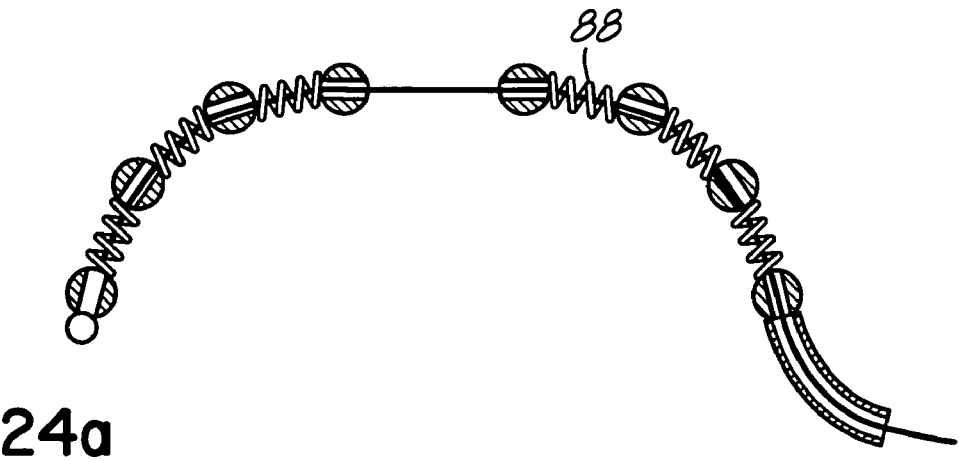
FIG. 24a-24b. Cross-sectional views of a set of rings with spacer compression springs and an actuating radial tether, shown both relaxed and actuated.
Figure 24B:
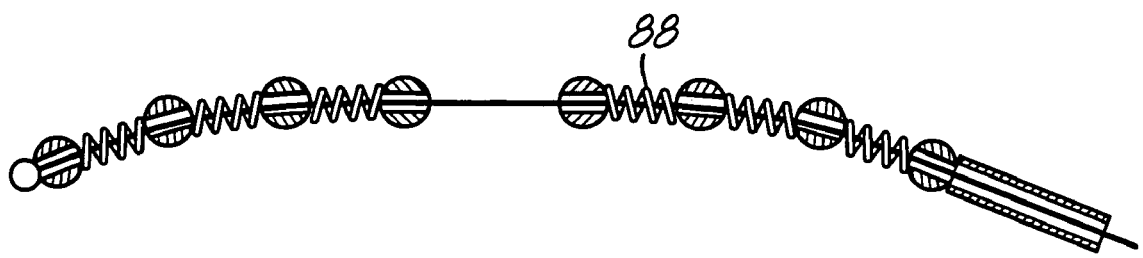

As an alternative to the eccentric traction tether mechanism, imposed curvature(s) required for these actions may be by any other method commonly used to induce curvature in a mechanical linkage, whether or not in medical devices.
   b. The solenoid-driven articulating link is illustrated in FIG. 12 and may be applied to an entire set of articulating links (as drawn) or to one or more regions of the set (preferred). A series of dumbbell shaped permanent magnet links [56] alternate with, and articulate with, double-socketed links containing solenoids [57] that may be either unactivated or activated. The permanent magnet links [56] have two heads [58], of any shape that is circular in the plane of bending (e.g., cylindrical, ellipsoidal, or spherical), and a waist [59]. Both solenoids and permanent magnets are completed by a housing [60] which is preferably of a very smooth, hard, and durable biocompatible material such as a ceramic. Each solenoid link is equipped with lead wires [6], which supply electric power. When unactivated (FIG. 24a), the solenoids have no polarity and the assembly assumes a shape dictated by the summation of extrinsic forces exerted against frictional and inertial impedance. However when (FIG. 12b) the solenoids are activated, an electromagnetic attraction/repulsion causes the solenoid links to rotate on the permanent magnet link ends toward a previously prescribed alignment and configuration as in FIG. 12b. The waist [4] of the dumbbells may be flexible, as in the pair of links [61] shown in FIG. 13 a, b, and c, if appropriate materials are selected for the permanent magnets [62], and elastically stiffened with spring elements [63], so that upon solenoid activation the heads [64] rotate in the solenoid housings [65] almost instantaneously. Because of mechanical impedance to deformation of the entire assembly (due to pressure in the underlying heart, stiffness of the jacket, and inertial forces) that deformation takes place much more slowly. Instead, the immediate effect of activation is elastic deformation of the waist of the permanent magnet links. The stored strain energy then effects a sustained force that gradually effects gross deformation of the entire mechanism as the flexurally elastic waists of permanent magnet appliances [63] re-straighten.

The physical characteristics of the permanent magnet and solenoid links may be interchanged as an alternative to the above. That is, for example, the permanent magnet links may be double socketed and the solenoid links double headed. Also, flexurally elasticity may be a characteristic of the solenoid links either instead of or in addition to the permanent magnet links.

As yet another alternative, variable inter-angulation of the solenoid and permanent magnet parts may be achieved by elastic bending connection rather than true articulation. This is illustrated in FIG. 14. Both parts are mounted on a flexurally elastic structure such as the non-limiting examples shown, one or more serpentine wire springs [66] and/or helical wire springs [67] of FIG. 14a. One of the various physical relationships that will be apparent to those knowledgeable in electromechanical design is illustrated. Solenoids [68], when unactivated, (FIG. 14b, c) allow the entire structure to assume a shape of equilibrium with extrinsic forces. When solenoids are activated, however (FIG. 14d, e) attraction or repulsion of the permanent magnets [69] cause the structure to bend in one or the other direction.

III. Relation of actuating unit to a flexurally elastic jacket, which incorporates wall-protecting members. This may be applied in two general configurations: (A) as a distinct structure from the jacket [51], although fixed to it, or (B) as a coherent, integral structure with the jacket [51]. One embodiment of a suitable jacket is the PCT application entitled "Deforming Jacket for a Heart Actuation Device," noted above and incorporated herein.

A. As a distinct structure from the jacket [51]. This configuration is implemented by first equipping the jacket's outer surface with any of the features described previously for epicardial protection, and then fitting with a separately constructed articulating link actuator. The actuator may be attached to the jacket [51]. at one or more points and slide over its protected surface in other sites. Thus the surface protecting features allow transmission of the normal force exerted by the actuator but not the shearing, potentially abrasive force, to the heart surface.

B. As a coherent, integral structure with the jacket [51]. Here, the jacket is constructed in a way that allows an improvement over the separate 'chain-of blocks' mechanism, in that the substance of the jacket may directly incorporate some or all of the components of an actuator of the articulating link or other type as an integral structure.

In a preferred embodiment of this mechanism illustrated above in FIG. 10, adjacent articulating links are held in apposition to each other by means of both being mounted on, and/or partially incorporated in, a portion of a flexurally elastic jacket [51]. The links [52] are mounted with the mounting region of the jacket under linear-tension such that when tension is released they are held in apposition by a compressive force determined by the mechanical characteristics of the jacket region and the elastic deformation achieved during mounting.

This allows free rolling articulation between the links within the angulation limits described above while preventing separation and dislocation of the shape-limiting elements in the presence of wall tension (due to heart chamber pressure) no greater than a predetermined allowable limit.

Actuators, which Work Primarily by Shortening.

Another class of actuator, a direct traction actuator shown in FIGS. 15-27 in various embodiments is applicable to any chamber. The primary action is shortening of one or more segments or regions of the chamber wall [70], rather than bending, This is an actuating mechanism for cyclically reducing the volume of at least one chamber of the natural heart by shortening, in at least one direction, at least one part of the wall [70] of the chamber, by cyclic traction and release on one or more traversing tethers [71]. One type of embodiment, the "concentric ring" actuator (shown later in FIGS. 20-27), is preferred for actuation of the right ventricle because the usual geometry of that chamber. That application is described in more detail below.

Tethers may be metal or polymer cables, chains, or any other form of flexible tension member known to those familiar with mechanical design. Tethers reach the heart by being enclosed in a flexible compression sheath [72]. At least one anchoring structure [73] is required, for mounting the end of the compression sheath relative to the heart. A second anchoring structure is required except in the event of a tether that traverses a closed loop path. Examples of anchoring structures are the limbs of the 'yoke' structure described in U.S. Pat. No. 5,957,977, or 'CardioClasp' passive ventricular reshaping devices, whether or not derivative of that patent, or portions of an active jacket.

Tethers may (currently preferred) traverse a series of floating elements held separated by springs which compress upon tether tightening to maintain relatively similar spacing between adjacent elements and between fixation structures that are relatively fixed to the heart and which provide end-anchoring and entry points for the tether. One example of discrete 'floating' element mechanism is the set of concentric rings having at least two tethers in different axes across the rings described below in more detail.

Figure 15A:
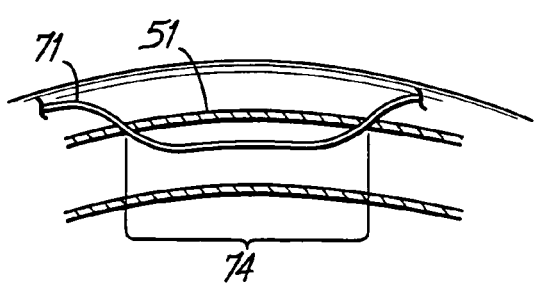
FIG. 15a-15b. Cyclically tightening purse string type of heart wall actuator in which a tether traverses a tunnel in and paralleling the surface of either the heart tissue itself or a compressible sheath or jacket outside the heart FIG. 16a-16b. Cyclically tightening purse string type of heart wall actuator in which a tether enters and exits, multiple times, either the heart tissue itself or a compressible sheath or jacket outside the heart FIG. 17a-17b. Tethers of the configuration of either FIG. 15 or 16, which enter through, and are stabilized by one or more anchoring framework structures on the heart surface.
Figure 15B:
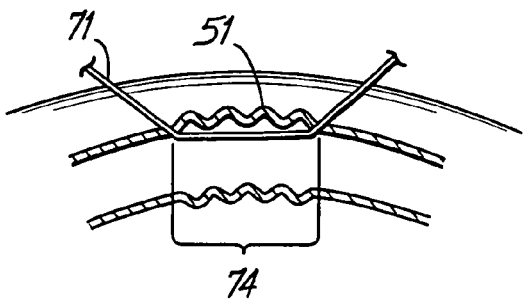

Tethers [71] may traverse a tunnel through either the native heart wall [70] or a compressible section of a sheath or jacket [51] that is external to the heart wall as shown in FIG. 15 *a* and *b* so that cyclic shortening of the traversed section [74], for any cause, effects cyclic shortening of that region of the heart or jacket in that direction.

Figure 16A:
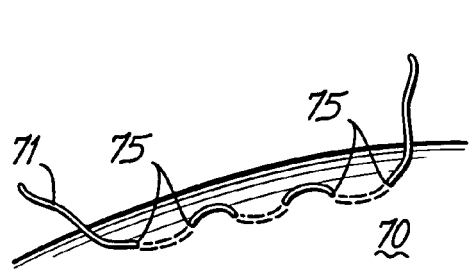
Figure 16B:
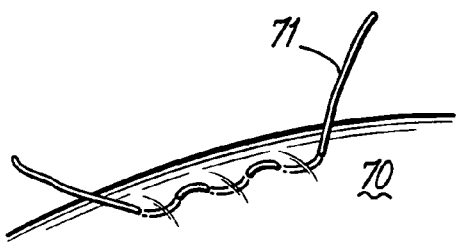

Tethers [71] may traverse a series of entry and exit points [75] in either the native heart wall [70] or a compressible section of a sheath or jacket [51] that is external to the heart wall in 'pursestring' fashion, as in FIG. 16 *a* and *b* so that cyclic shortening of the traversing section [3], for any cause, effects cyclic shortening of that region of the heart or jacket in that direction.

Figure 17A:
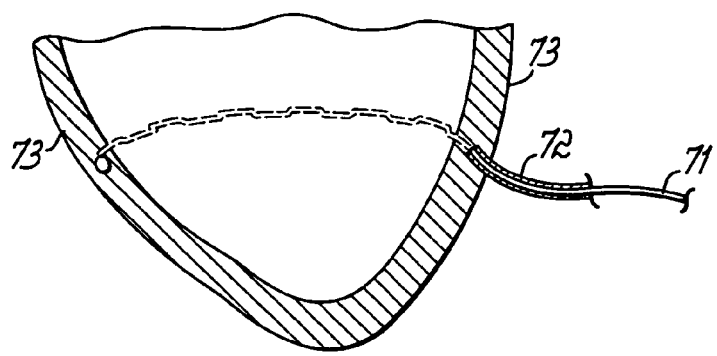
Figure 17B:
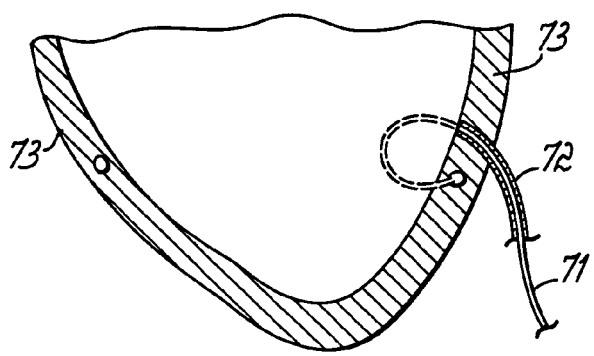

Tethers [71] may follow a path from a compression sheath [72], which is generally fixed to one anchoring structure [73] to a second anchoring structure [73] to which the tether itself is fixed as in FIG. 17 *a*. Alternately, tethers [71] may, in the event of a closed loop path, have their end fixation to the same anchoring structure [73] to which the compression sheath end is fixed as in FIG. 17*b*.

Figure 18A:
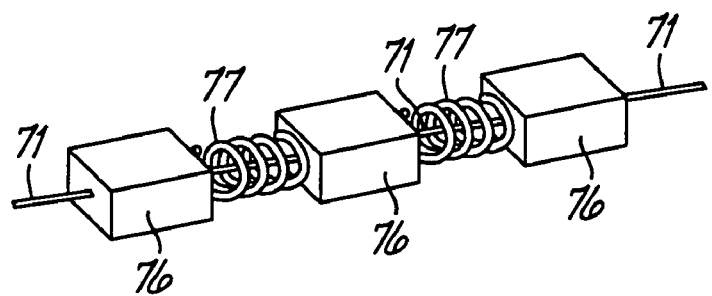
FIG. 18a-18b. Tethers, with or without anchoring structures such as in FIG. 17, which pass through a series of floating blocks on the heart surface, with blocks joined and separated by compression springs.
Figure 18B:
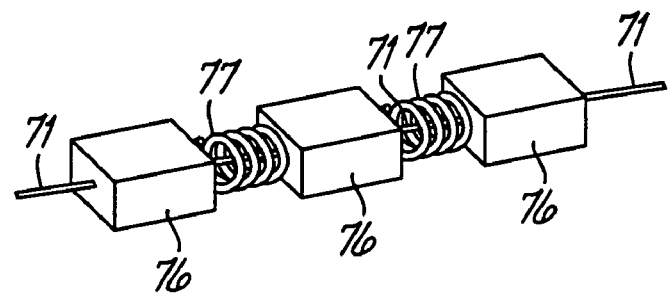

Tethers, with or without anchoring structures as described and illustrated in FIG. 17, pass through a series of floating blocks [76] which make up the local region of a heart jacket and which may be separated by spring elements [77] for the purpose of maintaining a similar relative distance between various pairs of adjacent blocks during cyclic actuation as is shown in FIGS. 18*a* and 18*b*.

Figure 19:
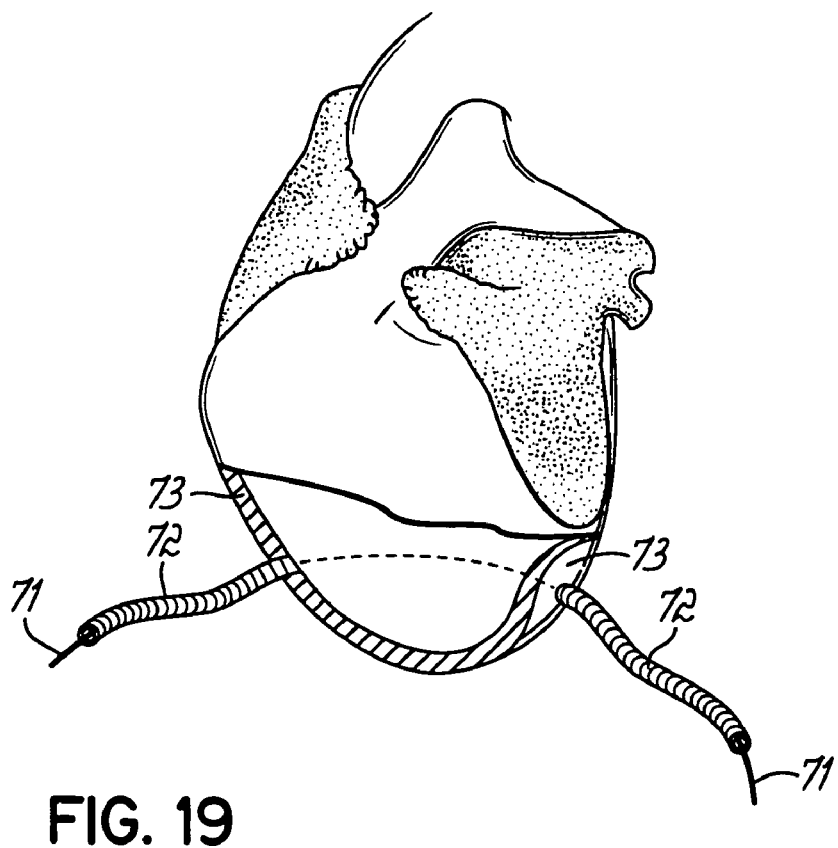
FIG. 19. A tether, acting on the heart wall by any of the mechanisms shown in prior figures, that is tensed by traction on either end through separate compression sheaths.
Figure 20A:
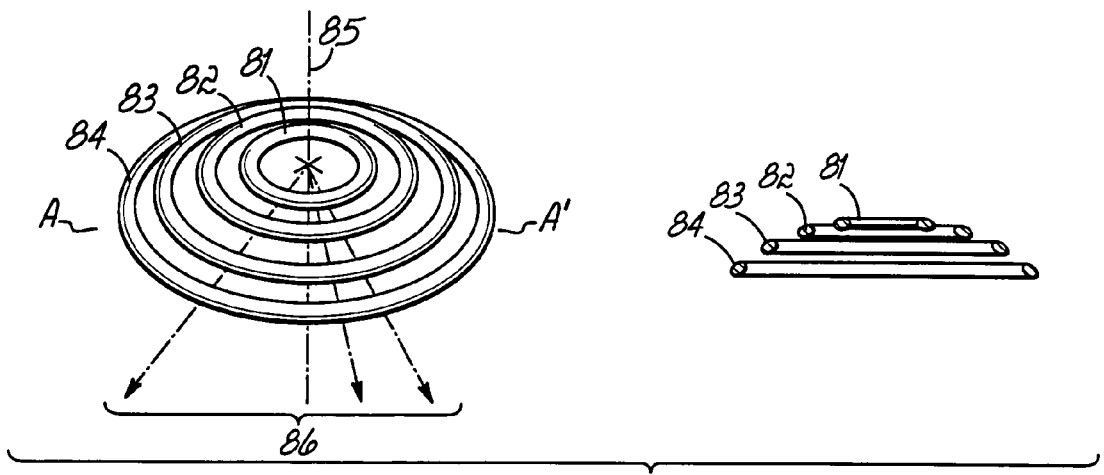
FIG. 20a-20b. A concentric ring actuator in which multiple tethers pass in different radial directions through a set of rings.
Figure 20B:
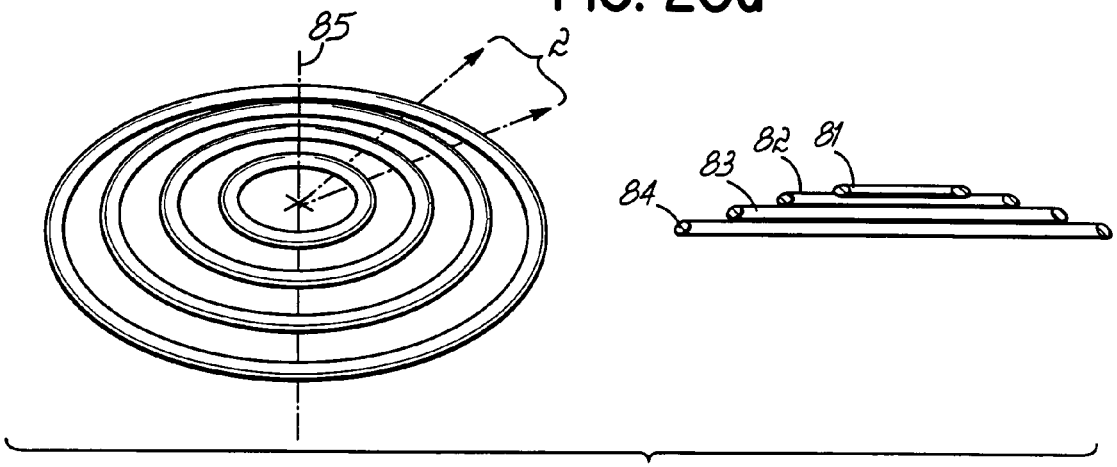

Tethers [71] may exit, and be actuated, through two compression sheaths [72], one on either end, each of which is fixed to an anchoring structure [73] as in FIG. 19.

The preferred embodiment of the direct traction actuator is the concentric ring actuator described as follows:

The purpose is to cyclically alter volume of a chamber of the heart, in situations where it's desirable for the affected area of wall to remain convex throughout the cycle. Example is the right ventricle [78], where the free wall can be induced to shorten and become somewhat less convex by such a mechanism as this. In that way, it will become closer to the septum [79], reducing chamber volume, without problems of wall coaptation that would be risked by applying curvature-reversing mechanisms, which are described principally for application to the differently-shaped (ellipsoid) left ventricle [80], to this anatomy.

Figure 21A:
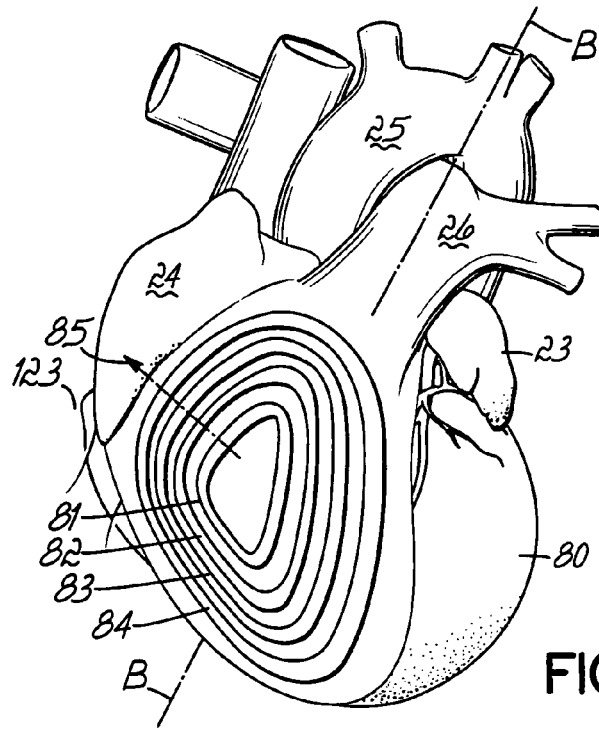
FIG. 21a-21c. The concentric ring actuator of FIG. 20, shown applied in a preferred embodiment, on the free wall of the right ventricle, in both perspective and sectional views.
Figure 21B:
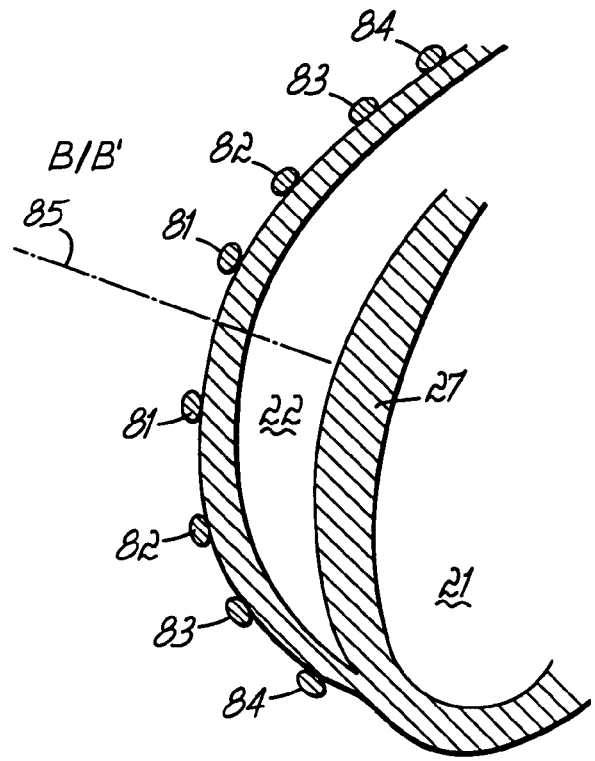
Figure 21C:
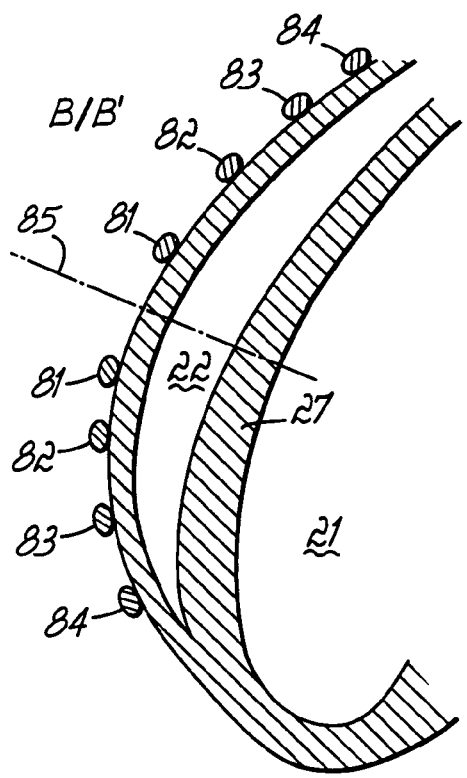
Figure 22A:
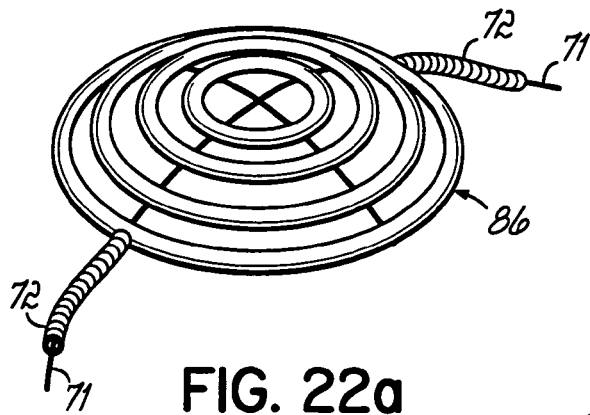
FIG. 22a-22d. Perspective view of a set of rings with tether-driven actuator mechanisms shown in relaxed and actuated states, each in both perspective and sectional views.
Figure 22B:
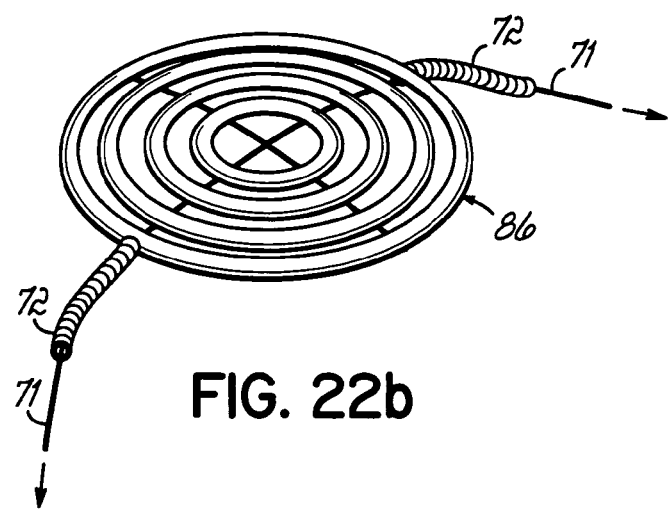
Figure 22C:
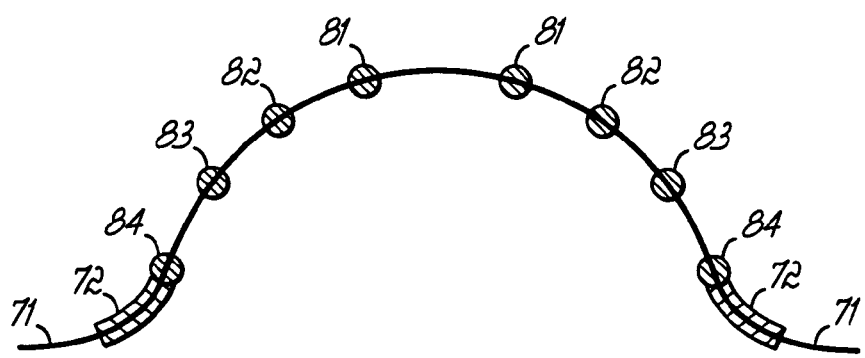
Figure 22D:
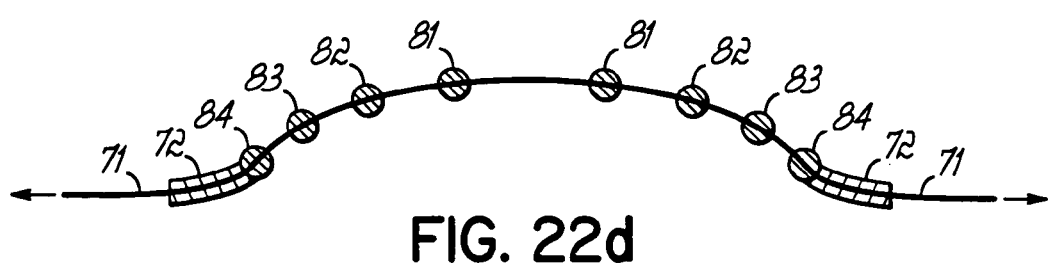
Figure 23A:
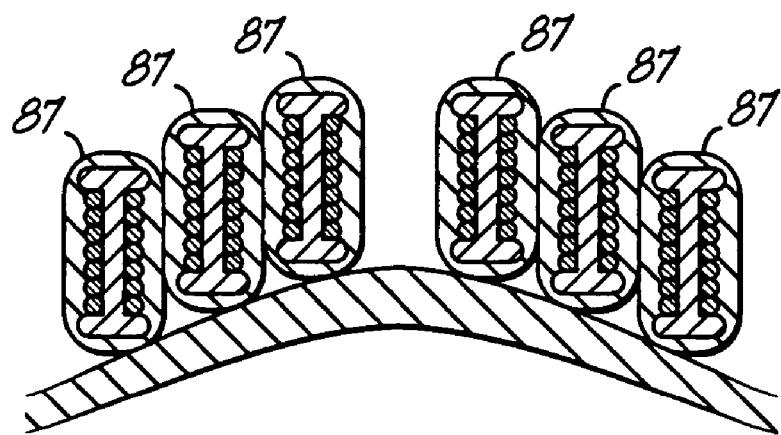
FIG. 23a-23b. Cross-sectional views of solenoids incorporated in a set of concentric rings, shown both in relaxation and in actuation.
Figure 23B:
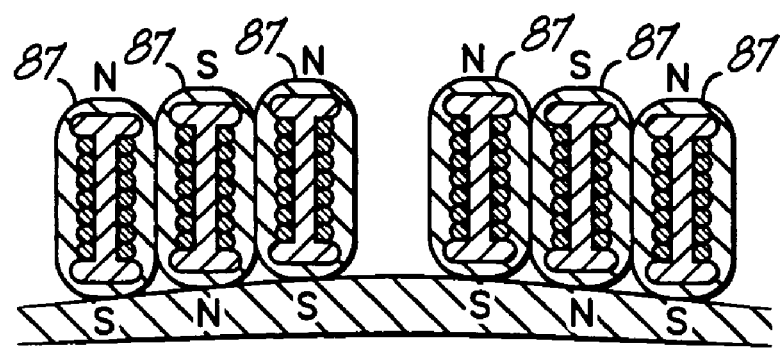
Figure 25A:
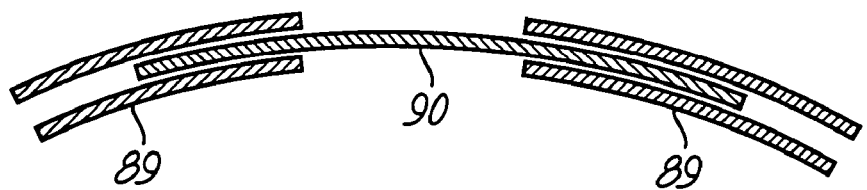
FIG. 25a-25b. Flexurally elastic telescoping axial brace in relaxation and in actuation FIG. 26. Heart with a preferred embodiment of the invention mounted on the right ventricular surface in a framework that is suitable for left ventricular actuating mechanisms as well.
Figure 25B:
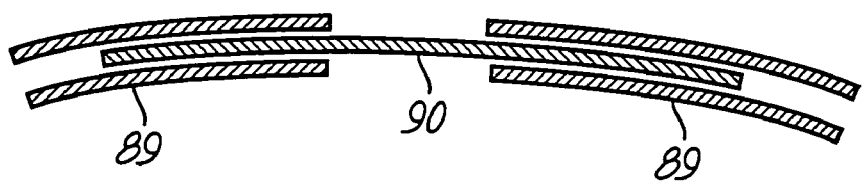
Figure 26:
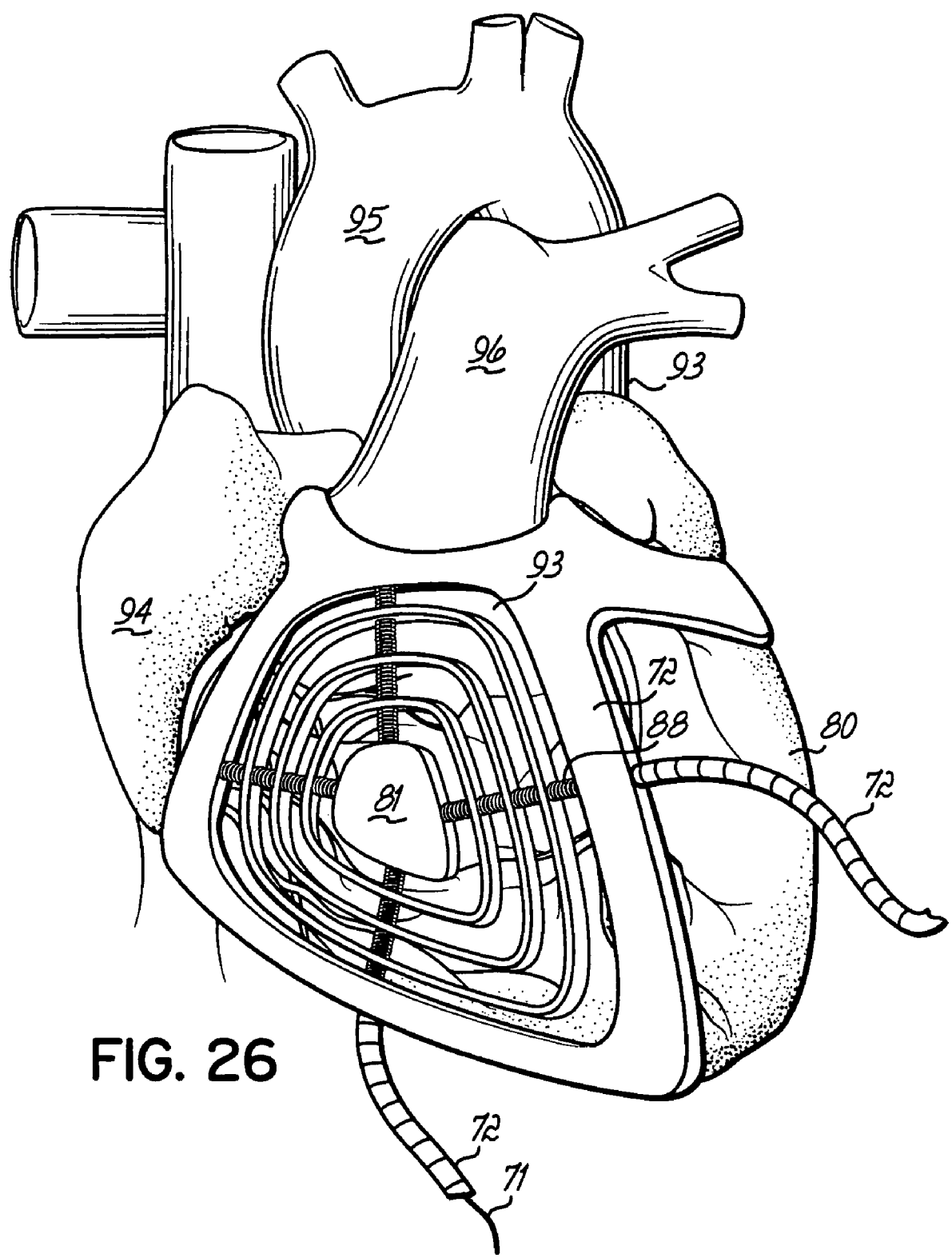

The assembly generally consists of:

a. At least one set of concentric rings [FIG. 20*a*] adjacent a surface, generally an external surface [FIG. 21*a*], of a heart chamber. The set may be of any number of rings; four rings [81-84] are shown in drawings only for convenient illustration. The innermost 'ring' [81] of the set may either a true ring (i.e., having an inner opening, as shown in drawings) or be a flat, convexoconcave or otherwise configured disc without such an inner opening. Each individual ring (such as a second [82], third [83] or fourth [84]) is not necessarily in a single plane (i.e., flat when viewed from its side) but may, rather, deviate from a single plane into a saddle-shape or other variation. As noted below, even when viewed from along the major axis [85] of the set, rings may be built in various shapes dependent on the cardiac anatomy that is to be deformed, and not necessarily be the roughly ellipsoid configurations illustrated in the drawings. That is, they may be circular, triangular with rounded corners, or any generalized closed loop configuration. Rings have at least some rigidity—i.e., are not totally flaccid—but may range from the near-absolute rigidity typical of most ceramics to the flexural elasticity typical of a polymer fiber/elastomeric matrix composite or torroidially-configured steel or titanium coil springs.

b. a mechanism for moving the rings relative to one another [FIG. 21*b*], such that reduction of chamber volume may be effected by movement of rings closer to the same plane [FIGS. 21*b*, 21*c*], and such that increase in chamber volume may be effected by the opposite movement. In general, principal movement of each ring will be in a direction parallel to the concentric axis [85] of the set of rings. This mechanism may be:

i. one or more [FIG. 22] tightening or loosening tethers [71] extending along a radial axis [86] through at least two and preferably all the concentric rings. A means of shortening the tethers such as the compression sheath [72] shown in FIG. 22, coupled with a driving mechanism (not shown, but understood by those familiar with mechanical design and described by us earlier in other disclosures for other heart-wall actuators) is required.

ii. activation of solenoids [87] (FIG. 23) incorporated in or mounted on the rings and preferably also of:

c. a means of ensuring that radial distances separating adjacent rings remain proportionate. For example, if the distance between the inner ring and next-to-inner ring decreases by 35% during actuation, the distance between the next-to-inner ring and the second-next-to-inner ring also decreases by approximately 35%. One example of such a mechanism (in the case of a tightening-tether actuation system in which a single tether actuates all rings along a radial axis [86] or along two opposite radial axes [86]) could be compression springs [88] separating adjacent rings along each such axis so that along any radial axis [86], as long as approximating force is equal, the reduction of distances will be proportionate. See FIG. 24.

d. A means of ensuring that displacement distance of adjacent rings (in the direction parallel to the central axis) is distributed smoothly. That is, for example, if the second ring [82] from center is displaced by 10 mm and the fourth ring [84] from center is displaced by 7 mm, the 3rd ring [83] from center should be displaced by roughly 8 to 9 mm, the 5th ring (if there is one) by 5 or 6 mm, etc. Examples are i. use of a common tether to approximate rings from the inner one to the most outer one along a specific radial axis. For example, using clock-face notation, if the specific radial axis of this particular tether were at 8 o'clock, then the '8 o'clock points' of each of the rings would tend to remain in a smoothly curved line with each other as the tether is tensed. If combined with relatively rigid rings, then intervening points between tethered radial axes would also be smoothly aligned. For example, if such tethers were at 7, 1, 10, and 4 o'clock radial axes, then use of rigid rings would ensure that not only points along those axes of the various rings, but also those along the 8 and 2 o'clock axes of the various rings, would be kept in relatively smoothly curved lines [FIG. 24].

ii. positioning of a flexibly elastic and linearly telescoping axial brace [89] with a sliding central core [90] along at least one radial axis [FIG. 25]

e. a means of ensuring that the general plane of each ring remains approximately perpendicular to the central axis of the assembly. This could be accomplished by balancing approximating forces at least three points, each less than 180 degrees from the other two, around ring circumferences. A preferred embodiment, combining some of the features noted above, is shown in FIG. 26. In this embodiment, parts of a 'yoke' or framework on the heart serves as both an additional outer ring and an anchoring point for two actuating tethers. These tethers each traverse two opposite radial axes (as shown, one [91] traverses axes at approximately 7 o'clock and 11 o'clock while the other [92] traverses axes at approximately 4 o'clock and 1 o'clock.

The central 'ring' [81] is actually a closed disc, convexo-concave shaped.

A continuous compression spring [88] runs along each of the four radial axes, surrounding the tether. It ends at the inner and outer ring and is fixed to each of the intervening rings.

There are 3 to 4 intermediate rings which are
   rigid,
   closed,
   round or ellipsoid in cross-section, and
   shaped to conform to concentric locations along a surface intermediate between the desired end-diastolic (most full) and end-systolic (most empty) configuration of the right ventricle ceramic or hard polymer bead-shaped bearings (not shown) surround the tethers inside the compression springs to allow metal-on-ceramic rather than metal-on-metal sliding friction; the bead material is chosen to minimize wear and maximize durability An alternative assembly employs tethers passing through all rings not in a radial direction, but obliquely. That is, one may pass, using clock face analogies, from 4 o'clock in the outer ring to 4:30 in the next, to 5 in the next, 5:30 in the next, and attach tangentially to the center ring or disc, and then exit progressively outward at 6:30, 7:00, 7:30, and 8:00 o'clock positions, respectively, whereas the second tether enters the outer ring at 2:00, and similarly passes obliquely to the center disc or ring at 12:00, exiting the outer at 10:00. This would have the advantage of requiring less length displacement for the same volume change than would a radial tether path, although more force would be required.

Figure 27A:
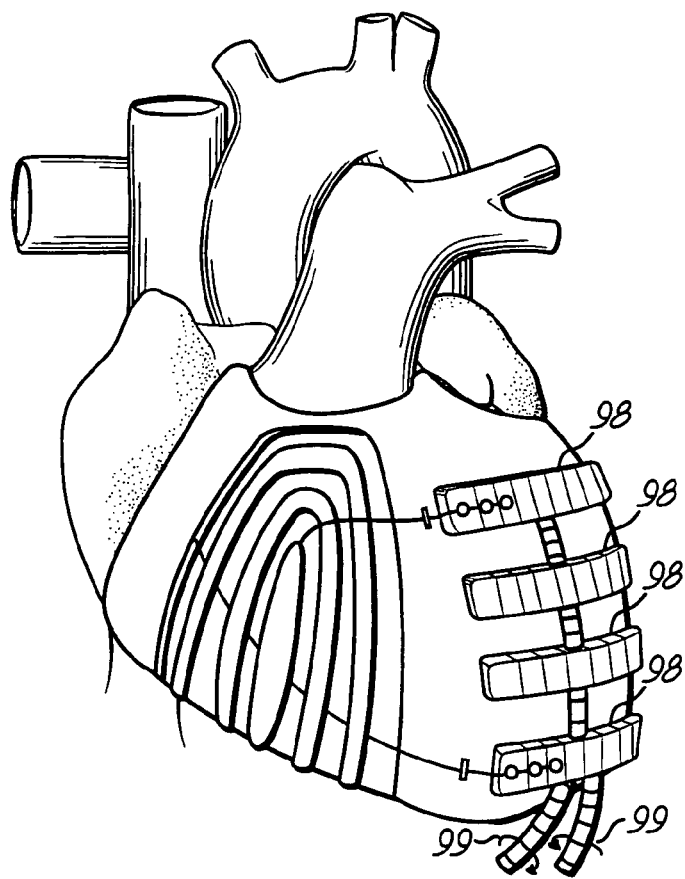
FIG. 27a-27c. A configuration for combining a preferred right ventricular actuating system the traction operated concentric ring assembly of FIG. 26m with a preferred left ventricular actuating system the torsion operated articulating link assembly of FIG. 8, in which the right ventricular system derives energy from the motion of the more powerful left system.
Figure 27B:
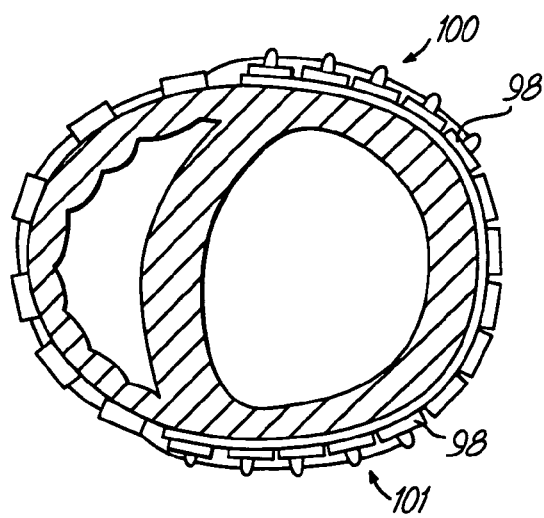
Figure 27C:
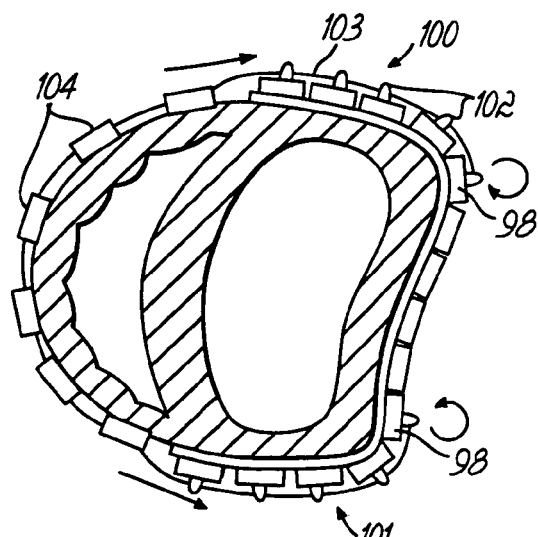

Combinations of Indenting Articulating Segment Actuators with Shortening Floating Block Actuators These two types of actuators may be used together, either independently driven or in an arrangement whereby one system, generally that of the higher pressured left ventricle, drives another, generally that of the lower pressured right ventricle. A nonlimiting example is that of FIG. 27. In this, a left ventricular actuator system of multiple transverse trains [97] of articulating links driven by torsion of junctional links [98] by two flexible shafts [99] causes the anterior segment [100] as well as the posterior segment [101] to become more acutely flexed, increasing distance between projections [102] on the links of those segments, tightening tethers [103] that then pass through sequential rings [104] of a right ventricular actuator. FIG. 27a is a perspective and FIGS. 27 b and c are sections of the heart in end-diastole and end-systole, respectively. The advantage over two independent systems is that in this example power must only be delivered directly to the left actuator.

While the present invention has been illustrated by a description of various embodiments and while these embodiments have been described in considerable detail, it is not the intention of the applicant to restrict or in any way limit the scope of the appended claims to such detail. Additional advantages and modifications will readily appear to those skilled in the art. The invention in its broader aspects is therefore not limited to the specific details, representative apparatus and method, and illustrative examples shown and described. Accordingly, departures may be made from such details without departing from the spirit or scope of applicant's general inventive concept.

What is claimed:

1. An actuation mechanism for assisting the operation of the natural heart comprising:
   a framework for engaging the heart;
   a plurality of individual, rigid links which are adjacent to one another to form a link assembly, the links articulating with respect to each other for varying the shape of the link assembly, the link assembly further including multiple regions wherein the links of one region articulate differently from the links of another region;
   the link assembly configured for being positioned proximate to an outer surface of the heart and the link assembly being fixed at least at one end to the framework;
   an actuator coupled to at least one of the links to change the angulation between the at least one link and an adjacent link and thereby deform the link assembly for deforming the heart.

2. The actuation mechanism of claim 1 wherein the links have rounded surfaces for rolling articulation.

3. The actuation mechanism of claim 1 wherein the links engage each other at least one of a cylinder-in-socket, a tongue-in-socket or ball-in-socket relationship for sliding articulation.

4. The actuation mechanism of claim 1 wherein the links are coupled together with flexing elements.

5. The actuation mechanism of claim 1 wherein the at least one link has a projection extending therefrom and an adjacent link has a depression therein, the projection engaging the depression when the links articulate with respect to each other.

6. The actuation mechanism of claim 1 wherein the at least one link has a hook extending therefrom and an adjacent link has a pin thereon, the hook engaging the pin when the links articulate with respect to each other.

7. The actuation mechanism of claim 1 wherein the actuator includes a mechanism for rotating at least one link for effecting articulation.

8. The actuation mechanism of claim 1 wherein the links of the one region are angularly constricted in articulation differently from the angular constriction of the another region.

9. The actuation mechanism of claim 1 wherein the links are coupled by a flexible tether, the tether sliding with respect to the links for varying the shape of the link assembly.

10. The actuation mechanism of claim 1 wherein the links are contained in a jacket.

11. The actuation mechanism of claim 1 wherein the plurality of links includes a plurality of permanent magnet links and a plurality of solenoid links articulating with the permanent magnet links.

12. The actuation mechanism of claim 11 wherein the permanent magnet links have two opposing ends coupled by a flexible waist.

13. The actuation mechanism of claim 1 wherein the links are coupled together with a flexurally elastic structure.

14. The actuation mechanism of claim 13 wherein the flexurally elastic structure is a spring.

* * * * *

UNITED STATES PATENT AND TRADEMARK OFFICE
CERTIFICATE OF CORRECTION

| | | |
|---|---|---|
| PATENT NO. | : 7,658,705 B2 | Page 1 of 1 |
| APPLICATION NO. | : 11/298430 | |
| DATED | : February 9, 2010 | |
| INVENTOR(S) | : Melvin et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 620 days.

Signed and Sealed this

Thirtieth Day of November, 2010

David J. Kappos
*Director of the United States Patent and Trademark Office*